US008628506B2

(12) United States Patent
Ales, III et al.

(10) Patent No.: US 8,628,506 B2
(45) Date of Patent: Jan. 14, 2014

(54) MULTIFUNCTIONAL MONITORING DEVICE FOR ABSORBENT ARTICLES

(75) Inventors: Thomas M. Ales, III, Neenah, WI (US); Andrew M. Long, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 944 days.

(21) Appl. No.: 12/164,961

(22) Filed: Jun. 30, 2008

(65) Prior Publication Data

US 2009/0326417 A1    Dec. 31, 2009

(51) Int. Cl.
*A61M 1/00* (2006.01)
*A61F 13/15* (2006.01)
*A61F 13/20* (2006.01)

(52) U.S. Cl.
USPC .................. 604/318; 604/358; 604/361

(58) Field of Classification Search
USPC ........ 600/584, 300, 301; 604/361; 340/573.1, 340/539.12, 573.5, 604, 605
See application file for complete search history.

(56) References Cited

U.S. PATENT DOCUMENTS

| | | |
|---|---|---|
| 3,486,166 A | 12/1969 | Campana et al. |
| 4,704,116 A | 11/1987 | Enloe |
| 4,940,464 A | 7/1990 | Van Gompel et al. |
| 5,058,088 A | 10/1991 | Haas et al. |
| 5,486,166 A | 1/1996 | Bishop et al. |
| 5,490,846 A | 2/1996 | Ellis et al. |
| 5,602,804 A | 2/1997 | Haas |
| 5,681,298 A | 10/1997 | Brunner et al. |
| 5,691,932 A | 11/1997 | Reiner et al. |
| 5,719,828 A | 2/1998 | Haas et al. |
| 5,766,389 A | 6/1998 | Brandon et al. |
| 5,785,354 A | 7/1998 | Haas |
| 5,820,973 A | 10/1998 | Dodge, II et al. |
| 6,167,362 A | 12/2000 | Brown et al. |
| 6,200,250 B1 | 3/2001 | Janszen |
| 6,250,929 B1 | 6/2001 | Kolb et al. |
| 6,417,455 B1 | 7/2002 | Zein et al. |
| 6,645,190 B1 | 11/2003 | Olson et al. |

(Continued)

FOREIGN PATENT DOCUMENTS

| | | |
|---|---|---|
| EP | 1393702 A1 | 3/2004 |
| EP | 1398014 A2 | 3/2004 |

(Continued)

OTHER PUBLICATIONS

International Search Report and Written Opinion, PCT/IB2009/052018, dated Jan. 26, 2010.

(Continued)

*Primary Examiner* — Brian Szmal
*Assistant Examiner* — H. Q. Nguyen
(74) *Attorney, Agent, or Firm* — Dority & Manning, P.A.

(57) ABSTRACT

Monitoring the status of an absorbent article can be desirable to various users in various situations. A monitoring device for use with an absorbent article is provided. The monitoring device includes a sensing device and a signaling device. The sensing device is configured to sense a physiological indication related to the absorbent article wearer. The functionality of the monitoring device may be updateable, for instance, by utilizing firmware updates, hardware or user interface changes, software installations, etc. Thus, the monitoring device of the present invention may be utilized over an entire lifespan from infants to elderly without the need for costly replacement or installation of an entirely new monitoring system.

20 Claims, 18 Drawing Sheets

(56) References Cited

U.S. PATENT DOCUMENTS

| | | | |
|---|---|---|---|
| 6,658,432 B1 | 12/2003 | Alavi et al. | |
| 6,705,972 B1 | 3/2004 | Takano et al. | |
| 6,752,430 B2 | 6/2004 | Holt et al. | |
| 7,222,732 B2 | 5/2007 | Ronn et al. | |
| 7,250,547 B1 | 7/2007 | Hofmeister et al. | |
| 7,280,441 B2 | 10/2007 | MacDonald et al. | |
| 7,295,125 B2 | 11/2007 | Gabriel | |
| 7,322,472 B2 | 1/2008 | Swiecicki et al. | |
| 7,330,818 B1 | 2/2008 | Ladocsi et al. | |
| 7,364,087 B2 | 4/2008 | Zimmer et al. | |
| 7,477,156 B2 | 1/2009 | Long et al. | |
| 7,489,252 B2 | 2/2009 | Long et al. | |
| 7,553,301 B2 * | 6/2009 | Suzuki et al. | 604/385.01 |
| 7,595,734 B2 | 9/2009 | Long et al. | |
| 7,829,181 B2 * | 11/2010 | MacDonald et al. | 428/203 |
| 7,885,855 B2 | 2/2011 | Kerth et al. | |
| 2002/0022523 A1 | 2/2002 | Dan et al. | |
| 2004/0220538 A1 | 11/2004 | Panopoulos | |
| 2005/0033250 A1 * | 2/2005 | Collette et al. | 604/361 |
| 2005/0137542 A1 | 6/2005 | Underhill et al. | |
| 2005/0156744 A1 | 7/2005 | Pires | |
| 2007/0135690 A1 | 6/2007 | Nicholl | |
| 2007/0149936 A1 | 6/2007 | Weber et al. | |
| 2007/0208232 A1 | 9/2007 | Kovacs | |
| 2007/0255241 A1 | 11/2007 | Weber et al. | |
| 2007/0270774 A1 | 11/2007 | Bergman et al. | |
| 2007/0282286 A1 | 12/2007 | Collins et al. | |
| 2008/0052030 A1 | 2/2008 | Olson et al. | |
| 2008/0082062 A1 | 4/2008 | Cohen et al. | |
| 2008/0082063 A1 | 4/2008 | Ales et al. | |
| 2008/0243099 A1 | 10/2008 | Tippey et al. | |
| 2008/0266117 A1 * | 10/2008 | Song et al. | 340/573.5 |
| 2009/0155753 A1 | 6/2009 | Ales et al. | |
| 2009/0295657 A1 | 12/2009 | Gakhar et al. | |
| 2009/0321238 A1 | 12/2009 | Nhan et al. | |
| 2009/0325221 A1 | 12/2009 | Long et al. | |
| 2010/0114046 A1 | 5/2010 | Ales et al. | |
| 2010/0155006 A1 | 6/2010 | Ales et al. | |
| 2010/0164733 A1 | 7/2010 | Ales et al. | |

FOREIGN PATENT DOCUMENTS

| | | |
|---|---|---|
| EP | 1309182 B1 | 12/2007 |
| JP | 2002 022688 | 1/2002 |
| JP | 2003 099278 | 4/2003 |
| JP | 2004 105668 | 4/2004 |
| JP | 2004 529730 | 9/2004 |
| JP | 2005 000602 | 1/2005 |
| JP | 2006 043389 | 2/2006 |
| JP | 2006 068466 | 3/2006 |
| JP | 2007 007352 | 1/2007 |
| JP | 2007 296024 | 11/2007 |
| WO | WO 00/37009 A2 | 6/2000 |
| WO | WO 2004/080296 A1 | 9/2004 |
| WO | WO 2005/008555 A1 | 1/2005 |

OTHER PUBLICATIONS

Supplementary Search Report dated Jan. 17, 2013, 6 pages.

* cited by examiner

MULTIFUNCTIONAL MONITORING DEVICE FOR ABSORBENT ARTICLES

BACKGROUND

Absorbent articles such as diapers, training pants, incontinence products, feminine hygiene products, swim undergarments, and the like typically include a liquid-permeable body side liner, a liquid-impermeable outer cover, and an absorbent core. The absorbent core is typically located in between the outer cover and liner for taking in and retaining liquids (e.g., urine, blood, etc.) exuded by the wearer. Various types of moisture or wetness indicators have been suggested for use in absorbent articles. For instance, conductive threads, foils, and/or other components can be included in one or more layers of the article. The threads, foils, and/or other components can be used to sense a change in an electrical characteristic or property which depends on wetness (or other condition(s)) of the garment.

For instance, the presence of urine or other wetness can be determined based on sensing a change in resistance, conductance, impedance, capacitance, and/or any other parameter or parameters. The device or devices used to sense the change in property or properties can produce a visual, audible, or other signal indicating a change in the condition of the absorbent article.

As an example, a pair of spaced apart parallel conductors may be situated within the absorbent material of an undergarment, with the conductors positioned to connect to a monitor included in or removable situated on the undergarment. The conductors may be configured to act as a voltage divider circuit, with the monitor detecting the wet/dry state of the undergarment based on the voltage level at a constant current. For instance, when the undergarment is dry, the circuit may act as an open circuit with practically infinite resistance, while the circuit may have a lower resistance when wet.

Monitoring of the status of an absorbent garment can be desirable to various users in many varied situations. For instance, the caregiver of an infant may be alerted to the condition of a diaper in order to change the diaper in an expeditious manner. A caregiver to a person with bladder or bowel control problems and/or user of an incontinence product may wish to be alerted to the presence of urine or other exudates for similar reasons. As yet another example, a caregiver using disposable absorbent training pants to toilet train a child may wish to know the status of the training pants for the purposes such as changing the pants when needed, tracking progress of toilet training, and providing guidance to the child during the oftentimes-stressful toilet training process.

Existing monitoring systems for absorbent articles are somewhat limited in user interface options. For instance, a monitoring device suitable for an infant would have various features and functionality that would not be appropriate or needed for an elderly incontinent user, for example. There exists a need in the art to provide an absorbent article monitoring device that is capable of being updated to "evolve" with the user to be applicable across various absorbent articles and various ages or training levels of the absorbent article wearers.

SUMMARY

In accordance with one embodiment of the present invention, a method for monitoring physiological indices in an individual as the individual ages is disclosed. The method comprises associating one or more signaling devices with absorbent articles worn by the individual. Each absorbent article includes at least one sensing device that senses a physiological indication related to the individual. The sensing device is placed in communication with the one or more signaling device when the absorbent article is being worn. The method further comprises inputting physiological information into the one or more signaling devices regarding the individual. At least one function or display of the one or more signaling devices may be changed as the individual increases in age.

The method may further comprise the step of recording information on the one or more signaling device received from the sensing device. The information may be stored on electronic storage medium. As the individual increases in age, the stored information may be used to change the at least one function or display. The at least one function or display changed may be changed by changing software, hardware, or firmware contained in the one or more signaling devices.

In one embodiment, the function of the one or more signaling devices is to indicate wetness in the absorbent article initially and then change to further indicate void frequency, void amounts, or an estimated wetness event as the individual increases in age. In another embodiment, the function of the at least one sensing device is to sense wetness in the absorbent articles initially and then change to detect anemia or the presence of a material including a yeast or a particular constituent in urine, menses, or blood. The constituent detected may be a polysaccharide, sugar, protein, or combinations thereof.

The one or more signaling device may be capable of being connected to an external device. The external source may be configured to change the software or firmware contained in the one or more signaling device. The external device may be connected to the external source utilizing a connection such as Bluetooth, radio-frequency identification (RFID), wi-fi (IEEE 802.11), ethernet, universal serial bus (USB), or combinations thereof.

In one embodiment, the method further comprises the step of connecting the one or more signaling device to a docking station, the docking station configured to charge a rechargeable cell in the one or more signaling device. The docking station may be configured for receiving software or firmware and changing the software or firmware contained in the one or more signaling device.

A monitoring device for use with an absorbent article worn by an individual is also disclosed. The monitoring device comprises at least one signaling device comprising hardware, software, firmware, or combinations thereof. The monitoring device further comprises at least one sensing device, the at least one sensing device configured to sense a physiological indication related to the individual. The at least one sensing device is electrically connected to at least one monitoring circuit in the absorbent article. The sensing device is in communication with the one or more signaling device. The monitoring device may further comprise an external device. The external device may be capable of receiving software or firmware. The external device may be configured to communicate with the at least one signaling device and change at least one function or display of the at least one signaling device as the individual increases in age.

An absorbent article is also disclosed. The absorbent article comprises a chassis comprising an outer cover. The outer cover has an interior surface and an exterior surface, and an absorbent structure positioned adjacent the interior surface of the outer cover. The chassis includes a crotch region positioned in between a front region and a back region. The absorbent article further comprises a monitoring device.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
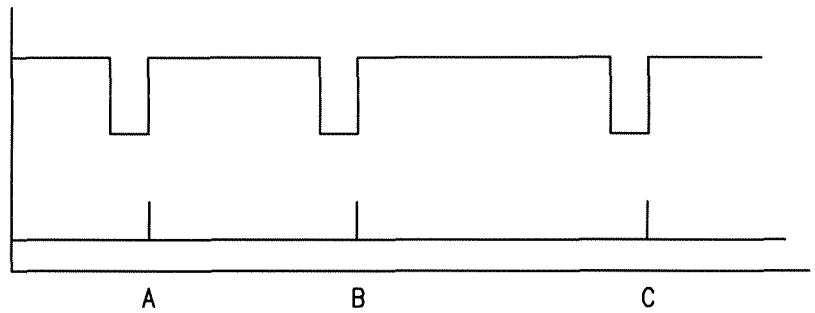
FIG. 1 illustrates a graph of two theoretical properties with time on the x-axis and a measurement of the electronic response on the y-axis.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

Embodiments of the present subject matter can be implemented and used in any suitable way. For example, a monitoring device can comprise a computing device or devices configured to receive inputs and provide outputs when in electrical communication with one or more circuits comprised by an article. The computing device can be configured by hardware, software, and/or firmware to provide various functionality. For instance, the computing device may comprise one or more microprocessors accessing stored instructions that configure the computing device to perform various tasks and respond to inputs. The instructions may be stored in any suitable medium or media. For instance, a microprocessor may interface with or include volatile and/or non-volatile memory comprising the instructions. However, software is not always necessary; functionality may be hardware-based. For example, the computing device may comprise customized hardware adapted to receive input and respond accordingly, such as an application-specific integrated circuit, microcontroller, or other suitable components and/or arrangements of components.

Additionally, the monitoring device may evolve over time to the user/caregiver stage of development/need. For example, monitoring device hardware or interface changes may be utilized to tailor to the specific needs of the user/caregiver. Furthermore, firmware may be programmed and updated, as needed, to change the functionality of the monitoring device to perform the desired functions. For instance, for newborns, the monitoring device may track wetness, void frequency and hydration. As the child enters the toddler stage, the monitoring device may evolve to record, for example, void amounts and frequency. Additionally, the monitoring device may be capable of accepting various inputs including inputs on diet, activity, age, etc. Based on the data inputted and recorded, the monitoring device may be capable of utilizing algorithms to create a predictive model that may assist, for instance, in potty training. As the child enters the adolescent stage, the monitoring device may evolve to include outputs such as anemia, hygiene, diet, activity, sun exposure, general health, etc. Additionally, the monitoring device may be utilized to indicate the presence of other material such as a yeast or a particular constituent in urine, menses, or blood, such as a polysaccharide, sugar, protein, etc. As adult stage is reached, the monitoring device may evolve to providing discrete indication to the user that an incontinent event, for instance, has occurred. Additionally, as the adult becomes more dependent, the monitoring device may be utilized to provide indication to a caregiver of such an event.

Furthermore, as age progresses, the functions or display may evolve accordingly. For instance, for newborns to toddlers, there may be no physical inputs/outputs (I/O's) on the device due to their limited motor skills and coordination. At ages later in development, there might be shapes or symbols that are activated to allow for basic development. For adolescents, gender appropriate I/O's would be required. For example, popular shapes, sayings, short hand, texting letters, etc. could be incorporated into the interface to allow for the adolescents to relate to the device, find utility in it, but still identify it as something familiar. For the elderly, I/O's would be simplified, for instance, to the absolute needs. For example, the buttons may be larger to allow those with bad eye sight to operate more efficiently.

In some embodiments, the monitoring device can comprise at least one sensing device, a first plurality of terminals, and a second plurality of terminals. The first plurality of terminals can be positioned to connect the sensing device to at least one monitoring circuit on an exterior surface of an absorbent article, while the second plurality of terminals can be positioned to connect the sensing device to at least one circuit internal to the article. In some embodiments, the sensing device can be configured to receive input data from a user of the article by monitoring for a change in a characteristic of the at least one external circuit. Input data can include information provided to the sensing device by a user of the garment, such as information to configure the monitoring device, select a mode of operation, direct the operation of the device, or respond to a prompt from the monitoring device. A "user" is meant to include any person(s) who interact with the article. This may include, for example, a wearer of the article, one or more caregivers who are responsible for supervising the wearer of the article (e.g. a parent or guardian or an infant), and/or any other persons responsible for overseeing the operation of the article (e.g. for a medical article worn by a patient, a "user" could include the patient and an attending physician, nurse, paramedic, etc.).

The sensing device can be configured to monitor the internal circuit(s) and provide at least one response based on monitoring for a change in a characteristic of the circuit(s). The response can be based on the input data, such as, for example a selected type or type(s) of feedback for specified conditions. For example, in some embodiments, the sensing device can be configured to support a plurality of modes, with each mode defining at least one type of response to be provided based on monitoring for a change in a characteristic of the internal circuit(s). User input data may select the mode of operation. For instance, a monitoring device may support different modes for different types of articles, with the type of article indicated by input data. As another example, a monitoring device may support different types of feedback indicating the condition(s) of the internal circuits and/or other status of the monitoring device. For example, the mode(s) may include a "silent" mode where no audible feedback is provided and at least one non-silent mode where audible feedback, such as music, tone(s), synthesized or recorded voice, or other sound-based output is provided.

In some embodiments, the monitoring device can be configured to prompt a user of the device for input. For instance, a user may be prompted to configure the monitoring device, select mode(s) of operation, specify conditions for feedback, etc. As another example, the monitoring device may prompt a user for input as part of a game. Generally speaking, a "game" refers to any suitable set of rules or parameters defining responses to be provided based on the input (or non-input) of data. For example, the monitoring device may provide a matching game, a fill-in-the-blank game, a trivia-game, game of chance, games that measure reflex times (e.g. where parameters define responses based on the time between a prompt to a user and the receipt of input data from the user), etc.

In some embodiments, the monitoring device is configured to store data in response to the received input data. For example, the monitoring device may include one or more memory chips, circuits, or hardware that facilitates storage of data. Alternatively, "storing data" can be achieved by providing the data to another device in communication with the monitoring device. In any event, in some embodiments, the monitoring device can store data indicating the status of at least one internal circuit over one or more time periods. For example, the frequency of internal conditions of the article, such as the occurrence or near-occurrence of wetness events (as inferred based on the status of one or more internal circuits) can be tracked for toilet training or medical care purposes.

In some embodiments, the monitoring device can provide feedback indicating the outcome of at least one component test. The component may be an internal component of the monitoring device, including, but not limited to, a feedback mechanism or other item connected to the sensing device, the sensing device, and/or one or more circuits connected to the sensing device. For instance, an article may include one or more circuits that correspond to a "test" command that can be used to verify the state of one or more connections between the monitoring device and the article and/or other aspects of the functionality of the article or monitoring device. The feedback can take any form or forms, including visual, audible, tactile, data transfer or storage, and/or other types of feedback.

The monitoring device may be configured to communicate with one or more external devices for feedback, configuration, and other purposes. For example, monitoring device may support connection using, for instance, BLUETOOTH-enabled devices, RFID techniques, Wi-Fi (IEEE 802.11) connection, and the like. Of course, data may be transferred to and from monitoring device 110 via other means, such as physical connection to other devices (e.g. Ethernet, a custom adapter, etc.) or through the use of removable media supported by monitoring device 110. User input data provided via one or more monitoring circuits formed on the exterior of the article may be used in facilitating/controlling communication with external devices.

In one embodiment, the monitoring device may assist in potty training. For instance, the sensing device may record and monitor the time when an insult takes place. Additionally, the sensing device may monitor and record when a series of insults take place. The monitoring may indicate that on four subsequent days insults took place at 7:00 p.m., 6:50 p.m., 7:10 p.m., and 7:02 p.m., respectively. Based on this information, the sensing device would predict that sometime between 6:50 p.m. and 7:10 p.m. an incontinent event may take place. This set of conditions indicative of a subsequent incontinent event, between 6:50 p.m. and 7:10 p.m., may then be communicated to the caregiver and/or the wearer. The caregiver and/or the wearer may be able to use this information to modify behavior to eliminate the incontinent event. In the case of a toddler, a caregiver may encourage the child to use the toilet about 6:45 p.m. The monitoring device may communicate to the caregiver visually, audibly, or via a cell phone, or other electronic device.

In another embodiment, the monitoring device may communicate to the caregiver and/or the wearer when the conditions indicative of a subsequent incontinent event occur. For example, using the above date, the monitoring device may activate at 6:40 p.m. indicating to the caregiver and/or the wearer for the wearer to use the toilet. The monitoring device may escalate the communication, either getting louder, or more frequent.

If monitoring device 110 is used in conjunction with multiple different absorbent articles, the caregiver/wearer of the articles may be able to assemble a data set of wetting (or other) events for use in determining the long-term status of the wearer. For example, in the potty-training context, the data may be used to predict likely times for accidents and/or overall progress. For instance, device 110 may be configured to forecast likely times of wetting events and provide an alert or notification to the wearer and/or caregiver. As an example, if multiple iterations of a wetting event occur at approximately 2:30 AM while a child is asleep, then the monitoring device may be configured to provide an alert shortly before 2:30 AM to awaken the child in time to go to the bathroom. For example, an audible and tactile alarm may be provided every morning at 2:25 AM until the tracking data indicates that accidents are no longer occurring at that time. Similar functionality can be provided in the context of other products, for example, an adult incontinence product to awaken an adult user before it is too late to reach a restroom. Additional exemplary aspects of predicting incontinent events are discussed in presently copending U.S. patent application Ser. No. 11/508,670, filed Aug. 22, 2006, entitled METHOD OF PREDICTING AN INCONTINENT EVENT, and Ser. No. 11/540,423, filed Sep. 29, 2006 and entitled TOILET TRAINING USING SENSOR AND ASSOCIATED ARTICLES, which are both hereby incorporated by reference herein to the extent such applications are not in conflict with the presently-discussed subject matter.

The monitoring device may electronically monitor more than just a property indicative of an incontinent event, such as a wet pant. For example the monitoring device may electronically monitor a second property which is indicative of the physical position of the body of the wearer, sitting, standing, lying prone, lying supine or lying on the side of the body. Changes in this property may be analyzed in conjunction with the property indicative of an incontinent event to determine if the wearer changes position in a predictable manner before a void. For example, the wearer may sleep generally on their back, but during lighter sleep patterns, they may roll onto their stomachs, which may then be correlated with an incontinent event. A device suitable to detecting body position is the HAAM-301B Piezo-Resistive 3-Axis Acceleration Sensor available from Hokuriku USA, Ltd. of Huntsville, Ala.

The monitoring device may electronically monitor a second property which is indicative of the physical activity of the wearer, for example stationary, restless, active, slightly active and very active. Changes in this property may also be analyzed in conjunction with the other properties described to determine if the wearer changes activity in a predictable manner before a void. For example, during periods of exciting active play, the wearer may become forgetful of the need to urinate. As activity decreases rapidly, an incontinent event may occur. Thus a pattern of decreased activity may indicate an incontinent event. Alternatively, parents may be familiar with the "potty dance" where the child makes smaller quick movements because of the urge to urinate. Here a pattern of increased activity may indicate an incontinent event. Further, perhaps a set time delay after waking may indicate an incontinent event. These activity levels also may be analyzed for patterns and correlated with incontinent events and be used as a prediction of a subsequent incontinent event. A device suitable to detecting activity level is the HAAM-301B Piezo-Resistive 3-Axis Acceleration Sensor available from Hokuriku USA, Ltd. of Huntsville, Ala.

The monitoring device may electronically monitor a second property which is indicative of the physical location of the wearer, for example longitude and latitude as determined by a GPS receiver. Changes in this property may also show patterns which may be indicative of incontinent events. For example, when the physical location of the wearer indicates that the child has been stationary in the kitchen or dining area, potentially eating or drinking, a pattern may develop that a given period after leaving the kitchen, an incontinent event may occur. Alternatively, the physical location of the wearer may indicate that the wearer is at home or at a daycare facility. Different patterns of drinking, activity, bathroom availability, etc. at these different locations may influence the patterns of incontinent events.

The monitoring device may electronically monitor a second property which is indicative of an intake of a substance by the wearer such a liquid, a solid, or a drug. For example this property may be data the wearer or caregiver may enter via a keyboard, mouse or touchpad indicating that the wearer has eaten, has drunk or has been given a drug. The property may be movement of the throat, which may be detected using a motion detector located on a necklace. A pattern may show that a given time after drinking an incontinent event may occur.

The monitoring device may predict conditions indicative of a subsequent incontinent event a number of ways. The monitoring device may compare the changes in the first and the second properties that are being monitored and compare them with known patterns predictive of incontinent events. Alternatively the monitoring device may look for individual incontinent events as indicated by the first property and then looked to changes in the second property which preceded the incontinent event. Upon finding an instance of a change in the second property followed by an incontinent event, the monitoring device may then compare other incontinent events for a similar cause and effect relationship. Multiple second properties may be compared to find more complex relationships and patterns.

FIG. 1 illustrates the graph of two theoretical properties with time on the x-axis and a measurement of the electronic response on the y-axis. The lower line indicates the response of the first property indicative of an incontinent event, specifically three incontinent events A, B and C. The upper line indicates the response of the second property. The response of the second property before the incontinent event indicates a decrease in the response shortly before an incontinent event, for example reducing activity (play) before urinating. This pattern may be predictive of a subsequent incontinent event.

Figure 2:
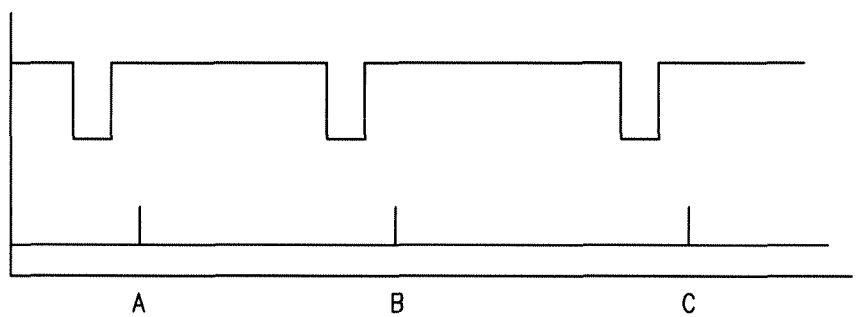
FIG. 2 illustrates an alternative graph of two theoretical properties with time on the x-axis and a measurement of the electronic response on the y-axis.

FIG. 2 illustrates a graph of two theoretical properties with time on the x-axis and a measurement of the electronic response on the y-axis. The lower line indicates the response of the first property indicative of an incontinent event, specifically three incontinent events A, B and C. The upper line indicates the response of the second property. The response of the second property before the incontinent event indicates a decrease in the response followed by an increase in the response shortly before an incontinent event. This pattern may be predictive of a subsequent incontinent event.

Figure 3:
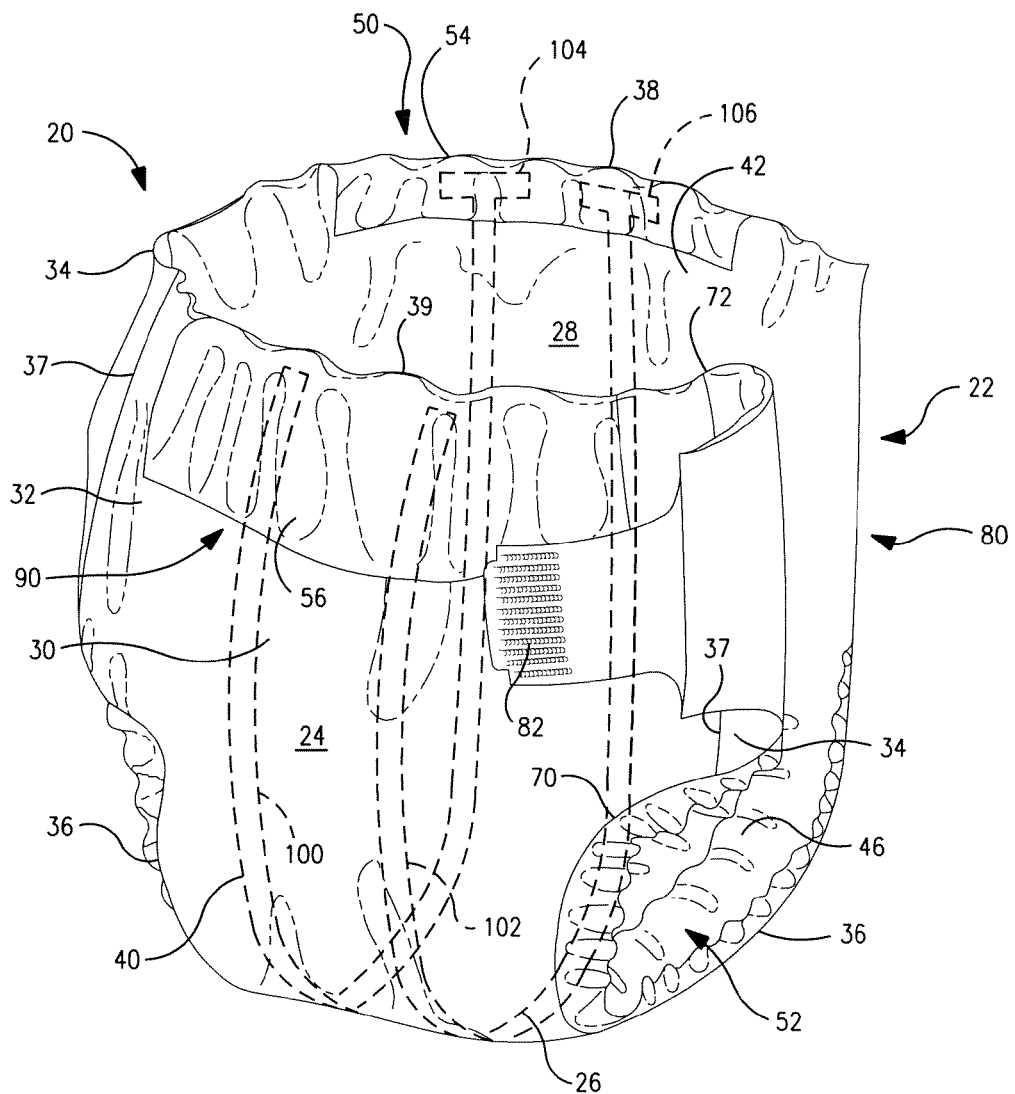
FIG. 3 is a rear perspective view of one embodiment of an absorbent article.
Figure 4:
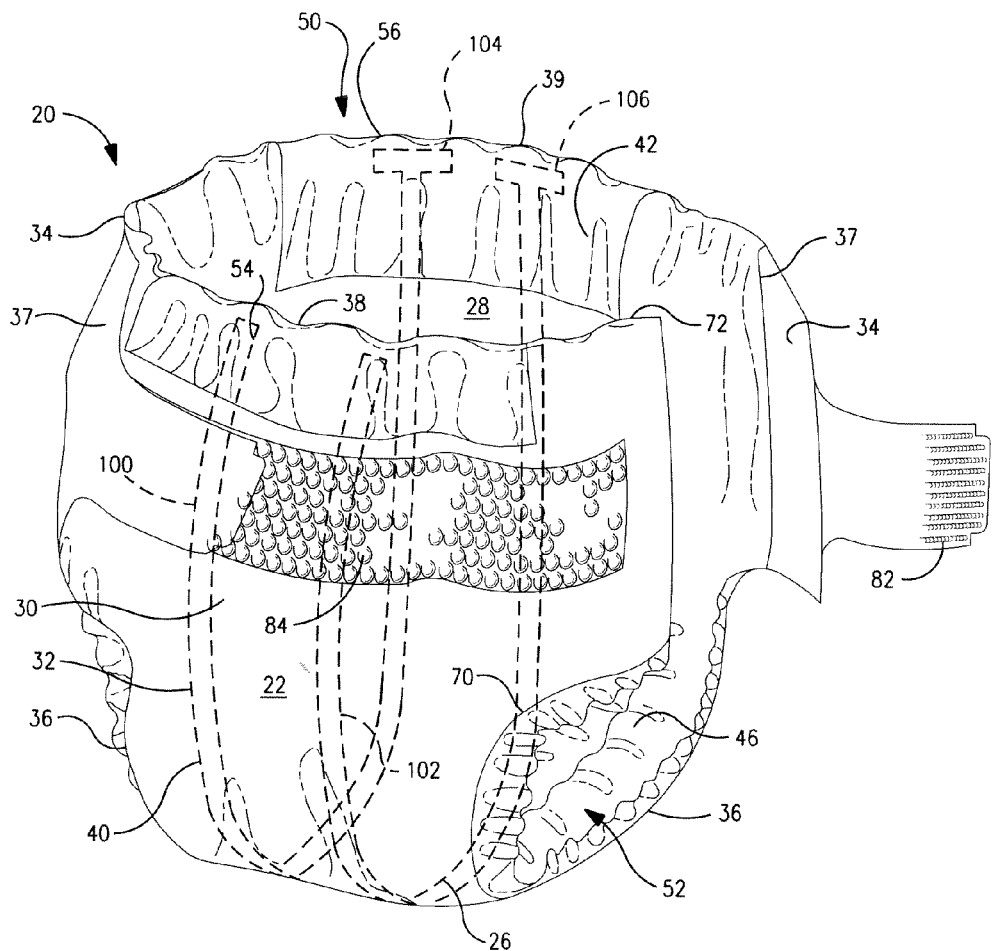
FIG. 4 is a front perspective view of the absorbent article illustrated in FIG. 3.
Figure 5:
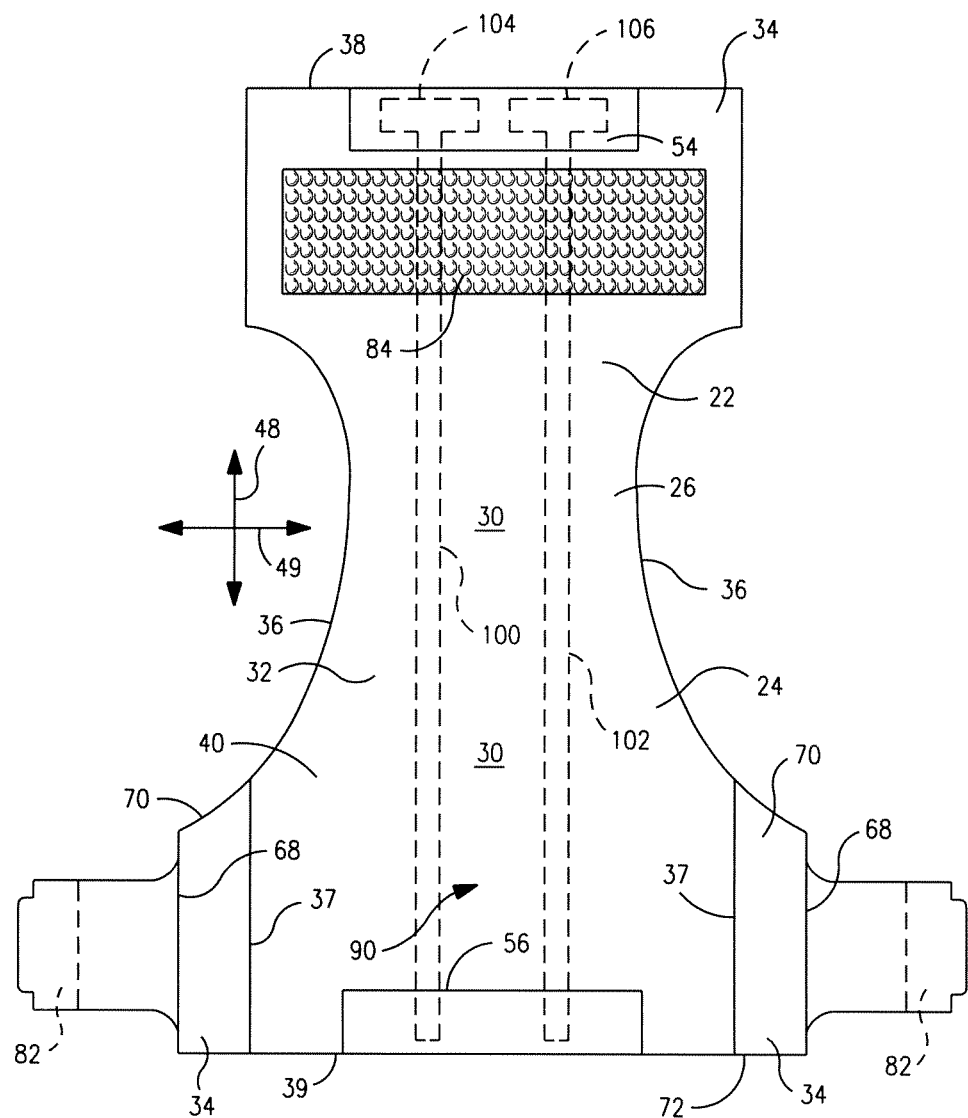
FIG. 5 is a plan view of the absorbent article illustrated in FIG. 3 with the article in an unfastened, unfolded and laid flat condition showing the surface of the article that faces away from the wearer.
Figure 6:
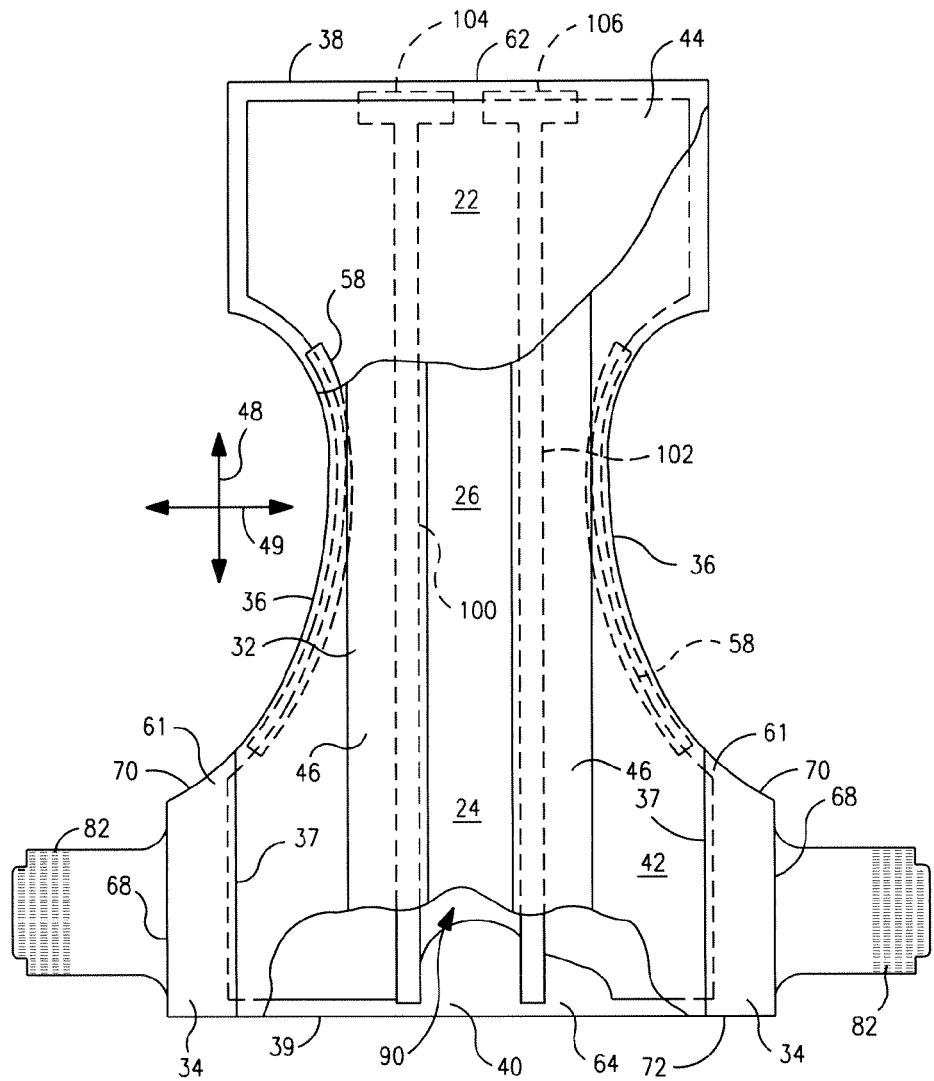
FIG. 6 is a plan view similar to FIG. 5 illustrating the surface of the absorbent article that faces the wearer when worn and with portions cut away to show underlying features.

An absorbent article 20 is representatively illustrated in FIG. 3 in a partially fastened condition. The absorbent article 20 shown in FIGS. 3 and 4 is also represented in FIGS. 5 and 6 in an opened and unfolded state. Specifically, FIG. 5 is a plan view illustrating the exterior side of the absorbent article 20, while FIG. 6 illustrates the interior side of the absorbent article 20. As shown in FIGS. 5 and 6, the absorbent article 20 defines a longitudinal direction 48 that extends from the front of the article when worn to the back of the article. Opposite to the longitudinal direction 48 is a lateral direction 49.

The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, which when worn, wholly or partially cover or encircle the waist or mid-lower torso of the wearer. The crotch region 26 generally is that portion of the absorbent article 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32 that, in this embodiment, encompasses the front region 22, the back region 24, and the crotch region 26. Referring to FIGS. 3-6, the chassis 32 includes an outer cover 40 and a bodyside liner 42 (FIGS. 3 and 6) that may be joined to the outer cover 40 in a superimposed relation therewith by adhesives, ultrasonic bonds, thermal bonds or other conventional techniques. Referring to FIG. 6, the liner 42 may suitably be joined to the outer cover 40 along the perimeter of the chassis 32 to form a front waist seam 62 and a back waist seam 64. As shown in FIG. 6, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 6 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 6 define a partially unattached edge which assumes an upright configuration in at least the crotch region 26 of the absorbent article 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 20 may also suitably include leg elastic members 58 (FIG. 6), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 3-6, the absorbent article 20 further includes a pair of opposing elastic side panels 34 that are attached to the back region of the chassis 32. As shown particularly in FIGS. 3 and 4, the side panels 34 may be stretched around the waist and/or hips of a wearer in order to secure the garment in place. As shown in FIGS. 5 and 6, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 3 and 4, the elastic side panels 34 may be connected by a fastening system 80 to define a 3-dimensional absorbent article configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the absorbent article 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 6, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is particularly directed to incorporating a monitoring device. The monitoring device may include a body fluid indicating system. One such system is described below. Other systems include a wetness liner such as that described in U.S. Pat. No. 6,658,432 to Underhill et al., a temperature system, a system in which graphics fade or appear, and any other suitable body fluid indicating system.

As shown in FIGS. 3-6, the absorbent article 20 includes a first conductive element 100 spaced from a second conductive element 102. In this embodiment, the conductive elements extend from the front region 22 of the absorbent article to the back region 24 without intersecting. The conductive elements 100 and 102 can comprise any suitable conductive material, such as a conductive thread or a conductive foil for example include 112-S silver metallic conductive paste (ink) from Electroscience Laboratories, Inc. and conductive foil described in U.S. Pat. No. 6,417,455 issued Jul. 9, 2002 to Zein et. Al. The first conductive element 100 may not intersect the second conductive element 102 in order to form an open circuit that may be closed, for instance, when a conductive fluid is positioned in between the conductive elements. In other embodiments, however, the first conductive element 100 and the second conductive element 102 may be connected to a sensor within the chassis.

The sensor may be used to sense changes in temperature or may be used to sense the presence of a particular substance, such as a metabolite. The particular targeted body fluid may vary depending on factors such as the particular type of article and desired application. For instance, an article/monitoring device may be adapted to detect the presence of urine or other wetness if the article comprises a diaper, training pant, adult incontinence product, or the like. As another example, the article/monitoring device may be adapted to detect the presence of a metabolite that would indicate the presence of a diaper rash. As another example, if the absorbent article comprises an adult incontinence product, feminine hygiene product, or surgical pad or garment, the absorbent article/signaling device may be adapted to indicate the presence of other material such as a yeast, particular constituent in urine, menses, or blood, such as a polysaccharide, sugar, protein, etc.

In the embodiment shown in FIG. 3, the conductive elements 100 and 102 extend the entire length of the absorbent article 20. It should be understood, however, that in other embodiments the conductive elements may extend only to the crotch region 26 or may extend to any particular place in the absorbent article where a body fluid is intended to be sensed.

The conductive elements 100 and 102 may be incorporated into the chassis 32 at any suitable location as long as the conductive elements are positioned so as to contact a body fluid that is absorbed by the absorbent article 20. In this regard, the conductive elements 100 and 102 generally lie inside the outer cover 40. In fact, in one embodiment, the conductive elements 100 and 102 may be attached or laminated to the inside surface of the outer cover 40 that faces the absorbent structure 44. Alternatively, however, the conductive elements 100 and 102 may be positioned on the absorbent structure 44 or positioned on the liner 42.

The conductive element 100 and 102 may be connected directly to a sensing device, either through direct or indirect contact. The first conductive element 100 may be attached to a first conductive pad member 104, while the second conductive element 102 may be connected to a second conductive pad member 106. The pad members 104 and 106 may be provided for making a reliable connection between the open circuit formed by the conductive elements to a sensing device that is intended to be installed on the chassis by the consumer or manufacturer. The pad members 104 and 106 may create a target zone for attaching the sensing device and the conductive leads or elements.

The conductive pad members 104 and 106 may have a relatively large surface area in relation to the conductive elements 100 and 102. For example, the conductive pad members 104 and 106 may have a surface area of at least 1 $cm^2$, at least 2 $cm^2$, and, in one embodiment, at least 3 $cm^2$. For instance, in one embodiment, the surface area of each pad member may be from about 2 $cm^2$ to about 4 $cm^2$.

The position of the conductive pad members 104 and 106 on the absorbent article 20 can vary depending upon where it is desired to mount the monitoring device. For instance, in FIGS. 3, 5 and 6, the conductive pad members 104 and 106 are positioned in the front region 22 along the waist opening of the article. In FIG. 4, on the other hand, the conductive pad members 104 and 106 are positioned in the back region 24 along the waist opening of the article. It should be appreciated, however, that in other embodiments, the absorbent article 20 may include conductive pad members being positioned at each end of each conductive element 100 and 102. In still other embodiments, it should be understood that the pad members may be located along the side of the article or towards the crotch region of the article.

The position of the conductive pad members 104 and 106 within the multiple layers of the chassis 32 may also vary depending upon where it is desired to connect the monitoring device and the type of attachment mechanism used to make a connection with the signaling device. As described above, the pad members 104 and 106 are electrically connected to the conductive elements 100 and 102. Thus, in one embodiment, the pad members 104 and 106 are positioned below (toward the body side) at least one layer of the outer cover 40. Positioning the pad members 104 and 106 below at least one layer of material may provide various advantages in some embodiments. For instance, locating the pad members 104 and 106 below at least one layer of material within the chassis 32 protects the pad members during shipping and storage and from forming a short circuit during use especially if the pad members are located adjacent one another. Another benefit to placing the pad members under at least one layer of material is the ability to easily manufacture the absorbent article 20 at high machine speeds.

It should be understood, however, that in other embodiments the conductive pad members 104 and 106 may be positioned at an exterior surface of the chassis 32. For instance, the pad members 104 and 106 may be positioned on the outside surface or on the inside surface as desired.

Figure 7:
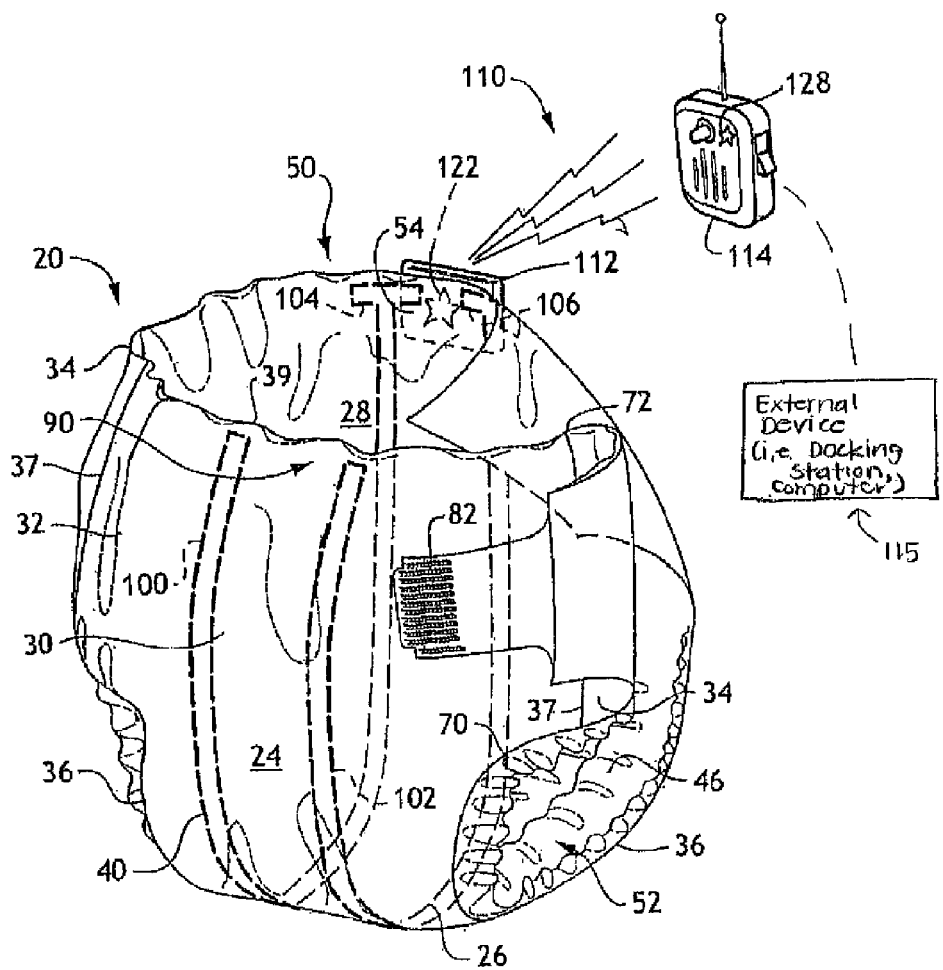
FIG. 7 is a perspective view of the embodiment shown in FIG. 3 further including one embodiment of a signaling device.

Referring to FIG. 7, for exemplary purposes, a monitoring device 110 (as depicted by ref. numerals 112 and 114) is shown attached to the conductive pad members 104 and 106. As shown, in this embodiment, the monitoring device generally 110 includes a sensing device 112 and a signaling device 114. The sensing device 112 includes a pair of opposing terminals that are electrically connected to the corresponding conductive elements. When a body fluid is present in the absorbent article 20, the open circuit formed by the conductive elements 100 and 102 is closed which, in turn, activates the monitoring device 110. In particular, in this embodiment, the sensing device 112 sends a wireless signal to the signaling device 114 which then indicates to a user that a body fluid is present in the absorbent article. However, in another embodiment, the sensing device 112 and signaling device 114 may be incorporated into the same body.

The monitoring device 110 can emit an audible signal or a visual signal in order to indicate to the user that the circuit has been closed. The audible signal, for instance, may be as simple as one or more beeps to perhaps emitting a musical tune. Similarly, if the monitoring device 110 issues a visible signal, the visible signal may comprise a few lights or an interactive display. In still another embodiment, the signaling device 114 of the monitoring device 110 may be configured to vibrate when the circuit within the absorbent article is closed.

In the embodiment shown in FIG. 7, the monitoring device 110 includes a sensing device 112 in combination with a signaling device 114. It should also be understood, however; that the monitoring device may comprise a single unit that remains attached to the absorbent article 20. For example, the monitoring device may be mounted on the absorbent article and issue a visible signal and/or an audible signal from the article itself. In addition, it should be understood that the signaling device 114 can be used in combination with an external device 115 via a connection such as Bluetooth, radio-frequency identification (RFID), wi-fi (IEEE 802.11), ethernet, universal serial bus (USB), or combinations thereof. The external device 115 can change the software or firmware contained in the signaling device 114. The external device 115 can be a docking station or other suitable device.

In other embodiments, the circuit can be configured so that a characteristic of the circuit changes when a user contacts the circuit. In some embodiments, each circuit may comprise a plurality of traces associated with a respective region on the exterior surface of the outer cover, with the traces arranged so that characteristic(s) of the circuit change when one or more traces are contacted by a user. In some embodiments, each region may correspond to at least a part of a feature visible at the outer cover.

In some embodiments, one or more absorbent articles can be provided to a user, along with one or more monitoring devices. For example, a kit or package may be provided that includes several absorbent articles, a monitoring device, and directions for use. A user can align a plurality of terminals of a monitoring device with a plurality of corresponding terminals carried on an absorbent article so as to place corresponding terminals in electrical communication with one another. Aligning can include positioning terminals connected to at least one external circuit formed at least partially on an absorbent article in electrical communication with corresponding terminals on the monitoring device. In some embodiments, aligning can include positioning terminals of at least one circuit located inside (or partially inside) the article in electrical communication with corresponding terminals on the monitoring device. The user can then provide data to the monitoring device by changing an electrical characteristic of one of the circuits in electrical communication with the monitoring device. Alignment may be aided in some embodiments, through indicia on the article and/or monitoring device, instructions included in the kit, and/or confirmation provided by the device that one or more circuits are connected.

Figure 8:
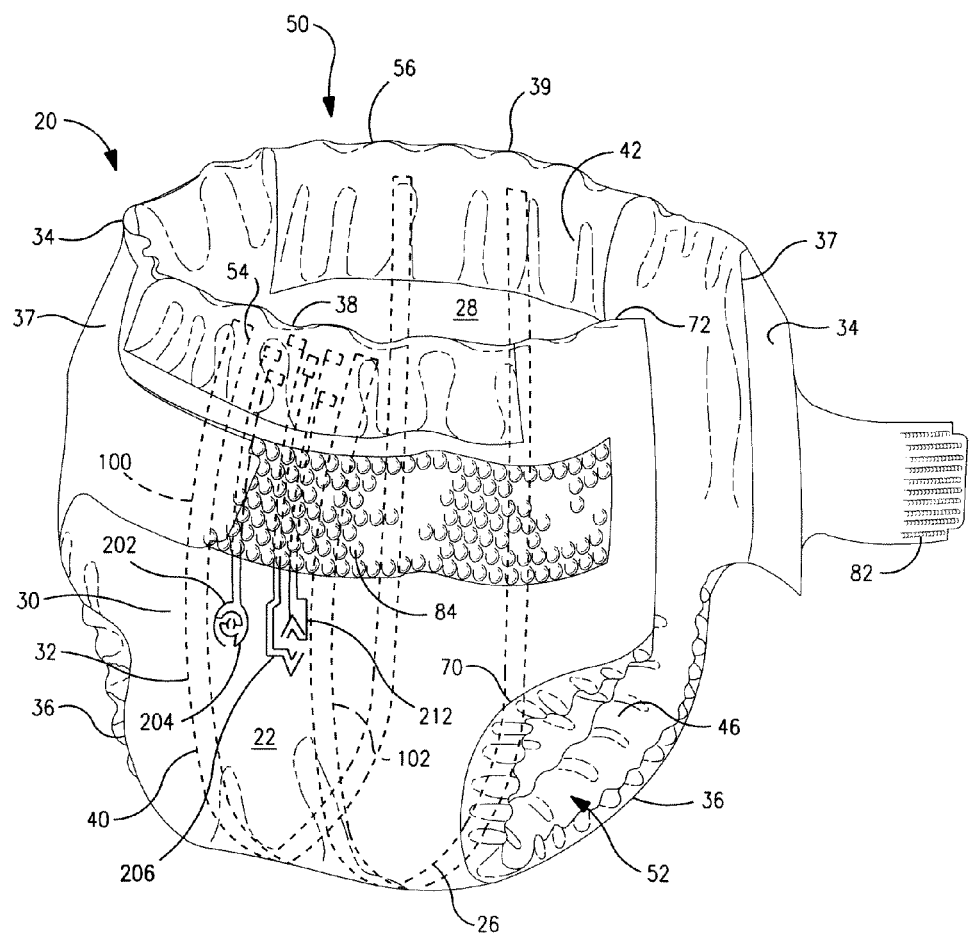
FIG. 8 is a front perspective view of an exemplary absorbent article in accordance with the present subject matter.

Referring to the example illustrated in FIG. 8, the absorbent article 20 includes three exemplary monitoring circuits that each comprise a pair of conductive traces formed at least partially on the exterior of article 20. The traces are also shown in closer detail in FIG. 8A, which is an enlarged view of a portion of the front side of article 20. Specifically, in this example, a first monitoring circuit comprises traces 202 and 204, a second monitoring circuit comprises traces 206 and 208, a third monitoring circuit comprises traces 210 and 212. The traces can be formed on the surface of the article in any suitable manner. For instance, conductive ink may be printed on the outer cover 40 prior to or after the cover material has been attached to other components of the article 20. Any suitable printing technique or techniques may be used. Also, other techniques may be used to apply or form conductive traces. Although shown in several figures herein as opaque, some or all of the traces may be fully or partially transparent. Furthermore, any suitable colors or combinations of colors may be used.

In this example, traces 202 and 204 form a button-shaped region and then each extend in the direction of waist edge 39. The portions of each respective trace in the button-shaped region may be printed in a conductive ink of one or more colors while the portion of each respective trace that extend up towards waist edge 39 may be transparent. Similarly, the ends of traces 206 and 208 form a "down" arrow-shaped region and the ends of traces 210 and 212 form an "up" arrow-shaped region. The arrow-shaped regions may be formed of non-transparent or semi-transparent ink while the remainders of the traces could be formed using transparent ink.

Of course, in some embodiments, all portions of the traces could be formed of transparent conductive ink, with various regions (such as the button and/or arrow-shaped regions) designated as input areas by visual indicia visible at outer cover 40. For instance, in this example, the area of outer cover 40 beneath the button-shaped region could have a corresponding visual feature coextensive with the button-shaped region formed by traces 202 and 204. The visual feature may be formed directly on outer cover 40 and/or may be formed elsewhere so as to be visible through outer cover 40.

Each trace 202, 204, 206, 208, 210, and 212 in this example extends in the longitudinal direction 48 towards waist edge 39. In this example, the dashed lines are used for purposes of clarity so as not to obscure fastening components 84 in FIGS. 8 and 9. However, the traces may be printed on cover 40 but below fastening components 84, may be below the cover in that area, and/or may be printed on fastening components 84.

In some embodiments, the ends of the traces are arranged to connect the circuits formed by the traces to respective terminals in a monitoring device 110 that can be attached to absorbent article 20. As is known in the art, a monitoring device can be removably (or permanently) attached to an article in a manner that components of the monitoring device are in electrical communication with electrical components in the article. "In electrical communication" can refer to a direct connection or an indirect connection, such as capacitive or inductive coupling, for instance. U.S. application Ser. No. 11/405,263 entitled CONNECTION MECHANISMS IN ABSORBENT ARTICLES FOR BODY FLUID SIGNALING DEVICES, filed Apr. 17, 2006, discusses several embodiments of connection mechanisms in absorbent articles for body fluid signaling devices. application Ser. No. 11/405,263 is hereby incorporated by references for all purposes herein to the extent it is not in conflict with the presently-discussed subject matter. Furthermore, the article and/or monitoring device may include one or more indicia, circuits, and/or other components to ensure proper alignment and attachment of the monitoring device 110 to the article.

In these examples, each trace is connected to a respective conductive pad area at the waist area of article 20. Specifically, trace 202 is connected to pad area 203, trace 204 is connected to pad area 205, trace 206 is connected to pad area 207, trace 208 is connected to pad area 209, trace 210 is connected to pad area 211, and trace 212 is connected to pad area 213. The conductive pad areas may be formed using conductive inks, as well and/or may comprise other conductive material (e.g. film, metal pad, etc.) positioned to form an electrical connection with the trace when the trace is printed on the cover.

Figure 8A:
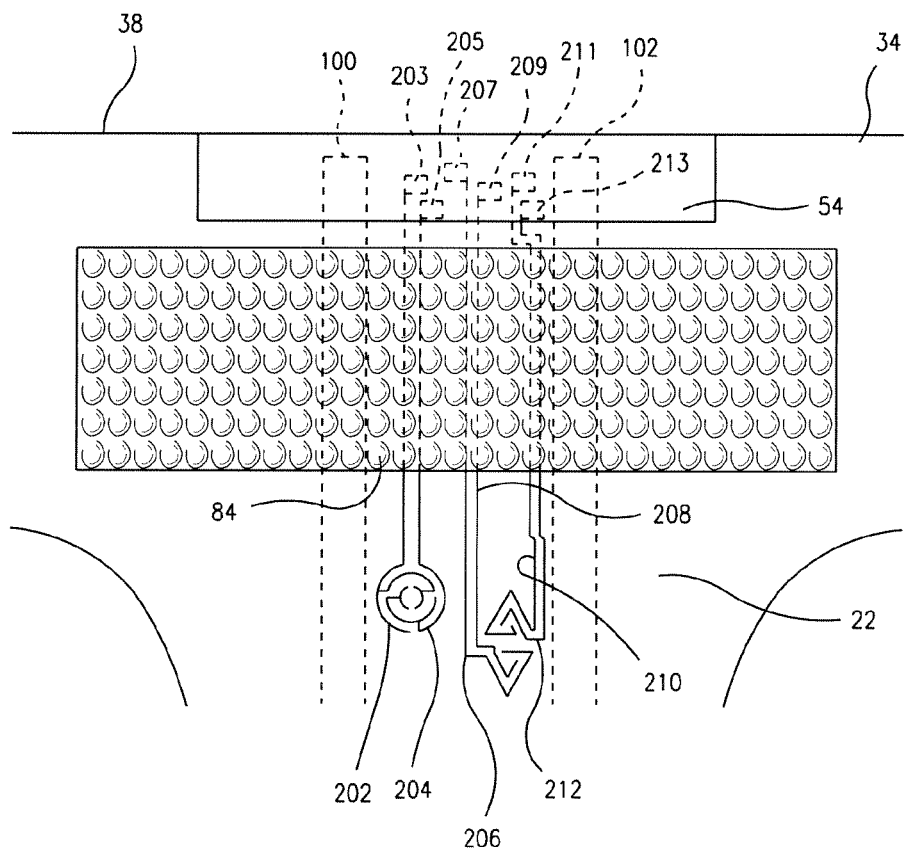
FIG. 8A is an enlarged view of the front portion of the exemplary article shown in FIG. 8.
Figure 9:
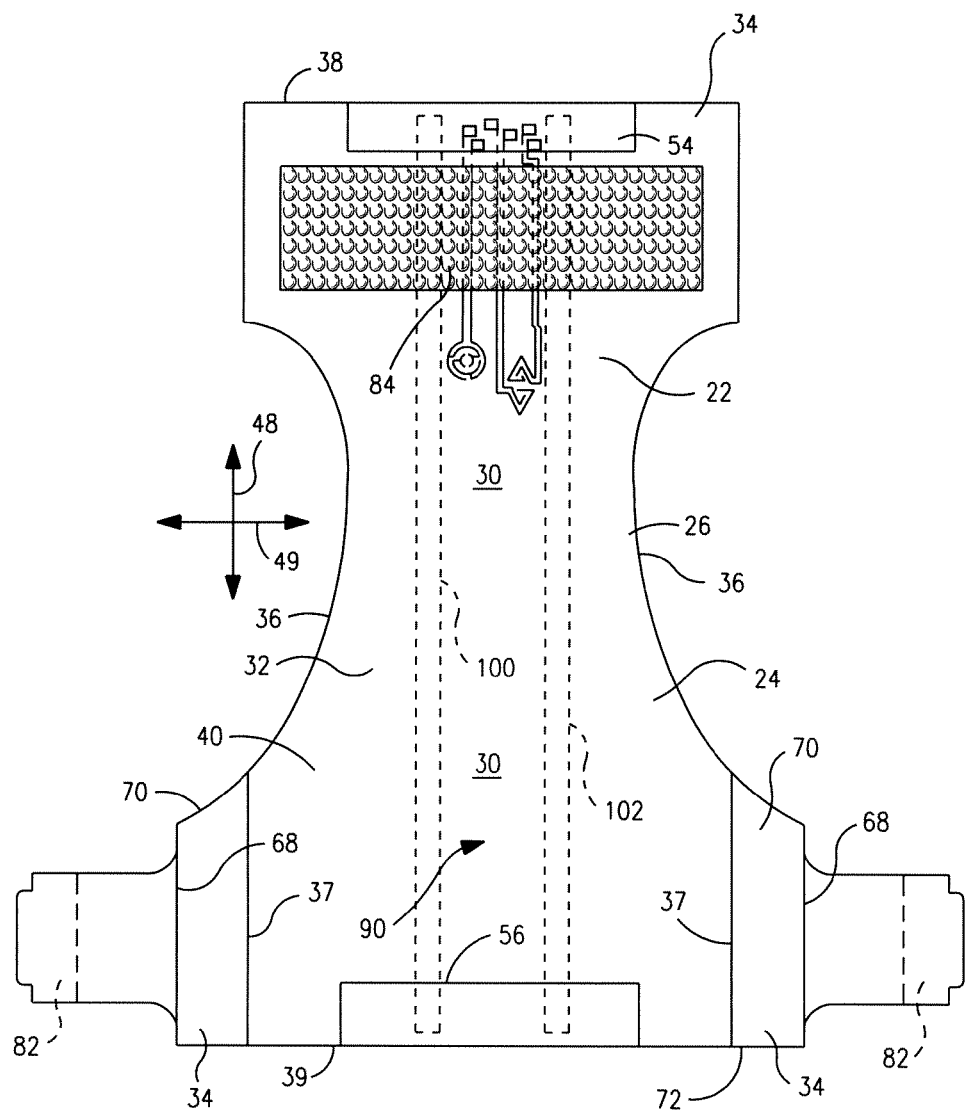
FIG. 9 is a plan view of the article shown in FIG. 8 with the article in an unfastened, unfolded, and laid flat condition showing the surface of the article that faces away from the wearer.
Figure 9A:
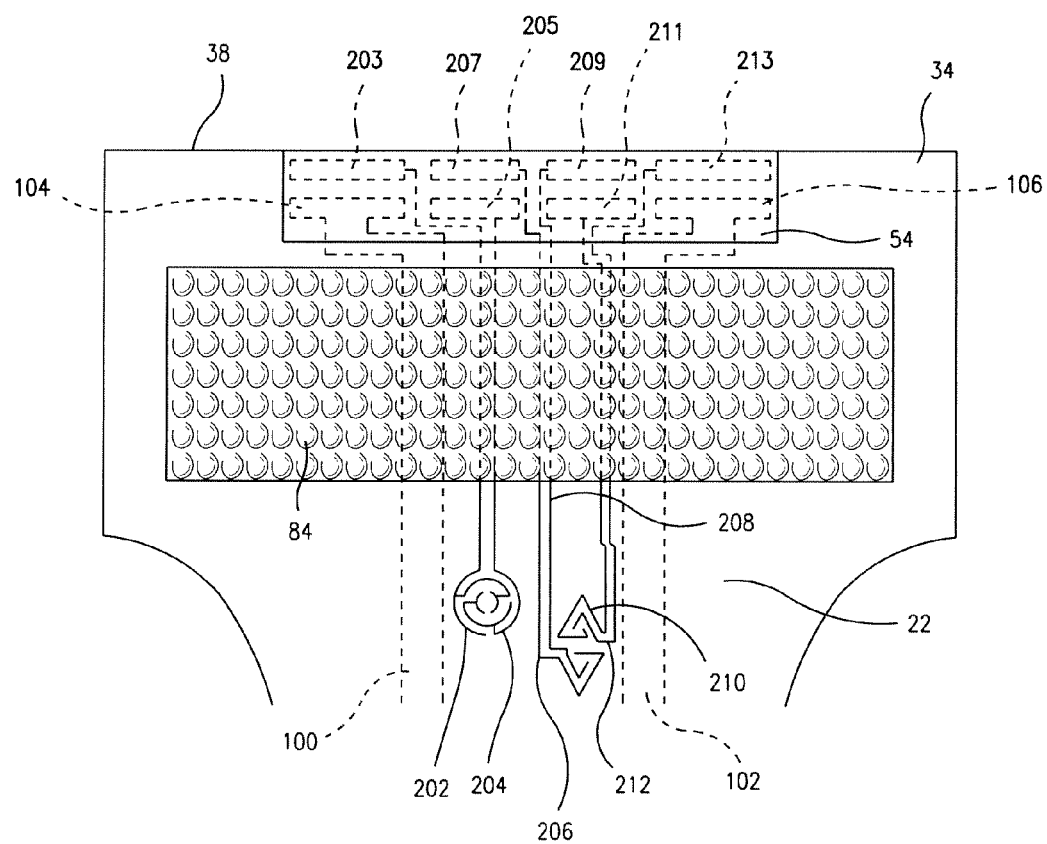
FIGS. 9A-9B are an enlarged view of the front portion of an article such as shown in FIGS. 8-9 but featuring a different exemplary arrangement of conductive pad members.
Figure 9B:
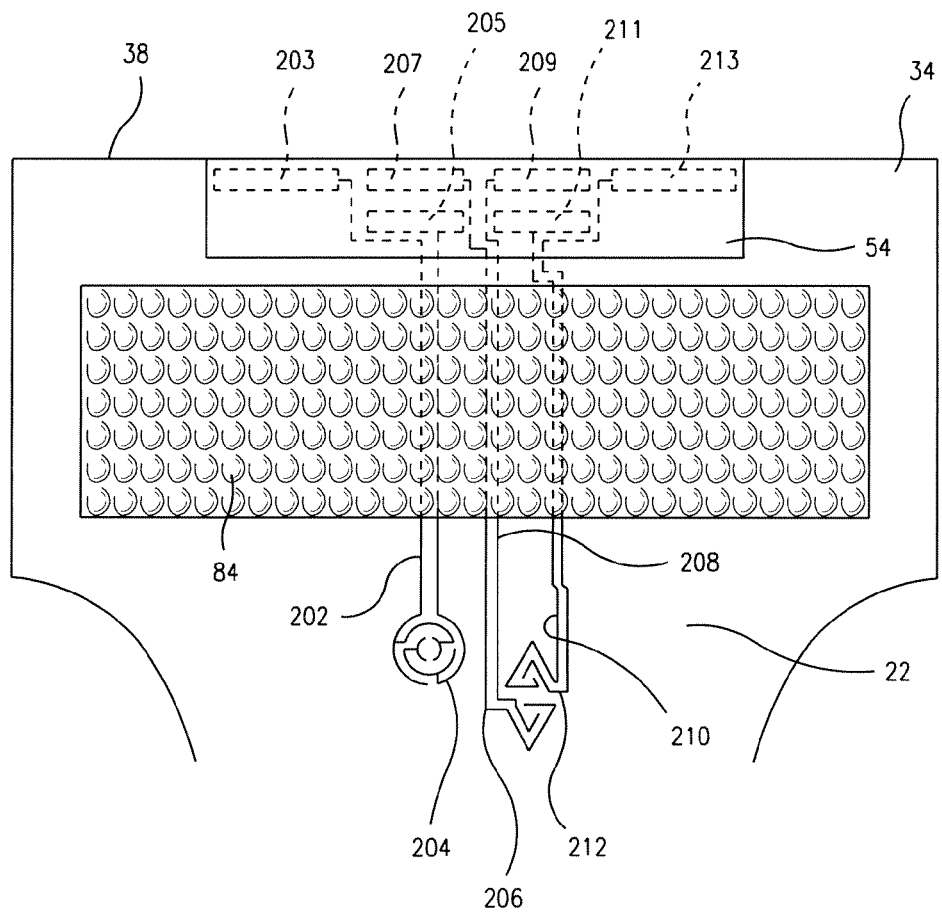

In the example of FIGS. 8, 8A, and 9, conductive elements 100 and 102 are shown without pad areas. However, in alternative embodiments, elements 100 and 102 may include respective pad areas as well. For instance, FIG. 9A illustrates an enlarged view of an article such as shown in FIGS. 8-9 but including conductive pads 203, 205, 207, 209, 211, 213 for each respective conductive trace 202, 204, 206, 208, 210, and 212. FIG. 9A is an enlarged view of the front side of the article as indicated by the oval; note that the non-enlarged view does not illustrate the full detail of the article. Furthermore, in this example, conductive pads 104 and 106 are shown for connection to elements 100 and 102, respectively. FIG. 9B is another view of the article shown in FIG. 9A. However, in FIG. 2B, only the traces for external monitoring circuits and associated pads are shown for purposes of clarity.

It is to be emphasized that the depiction in the Figures of traces, conductive pad areas, conductive elements, and the like in different sizes and arrangements is for purposes of example only. The figures are not to scale and it is not intended to limit the present subject matter based on the relative sizes (or other aspects) of the traces, conductive pad areas, conductive elements, and other components shown in the Figures. For instance, conductive elements 100 and 102 are each depicted by a pair of spaced apart dashed lines, while traces are depicted as single dashed (or solid) lines. Although in several embodiments, traces may be narrower than conductive elements, the conductive elements may be narrower than traces in other embodiments. In still further embodiments, traces and conductive elements may be of comparable width. Additionally, for purposes of clarity, traces are shown in the examples as spaced apart from conductive elements. However, in some embodiments, traces may be at the same location relative to the top, bottom, or sides of the article as conductive elements, but with the traces located on the exterior of the article and separated from conductive elements by one or more layers or components of the article. Similarly, conductive pads for conductive elements and traces may be located at the same location on the article, but at different layers, depending on the connection mechanism(s) associated with monitoring device(s) used with the article.

Figure 10:
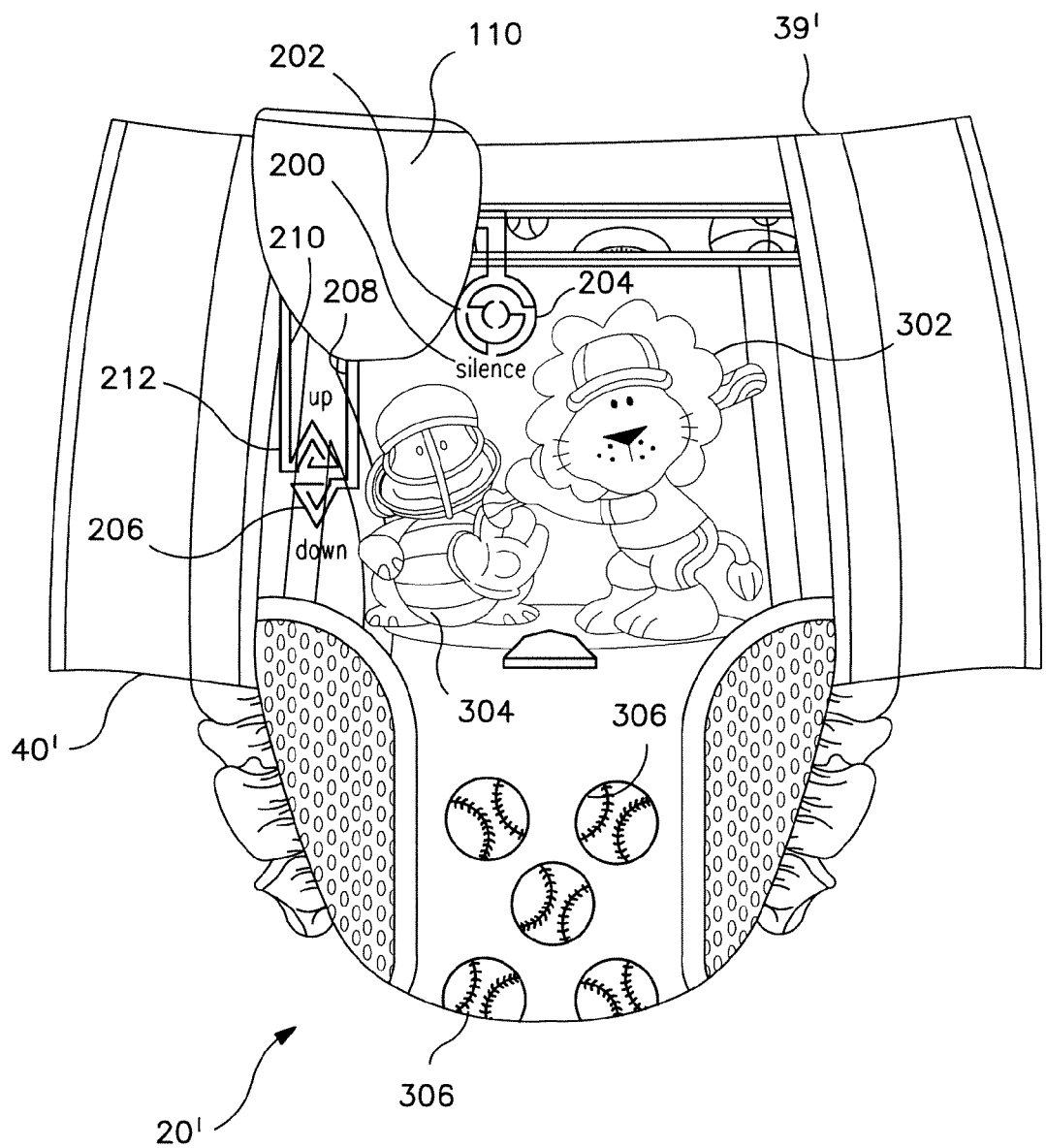
FIG. 10 is a front view of another exemplary absorbent article made in accordance with the present subject matter.

Turning briefly to FIG. 10, another exemplary absorbent article is shown, in this example, a training pant 20'. FIG. 10 depicts a front side exterior view of training pant 20' with a monitoring device 110 positioned on the article. The exemplary training pant 20' shown in FIG. 3 also includes three monitoring circuits formed on the exterior surface of outer cover 40', the circuits comprising traces 202 and 204 arranged in a button-shaped area, traces 206 and 208 arranged in a "down" arrow shape, and traces 210 and 212 arranged in an "up" arrow shape, respectively. Each trace further extends in the longitudinal direction 48 towards waist edge 39' for connection with monitoring device 110.

Monitoring device 110 can comprise any suitable arrangement of components that are configured to sense user interaction with monitoring circuits and provide a response. For instance, monitoring device 110 can comprise one or more sensing devices, such as a microprocessor and related components, such as a current source (e.g., a battery) and a plurality of terminals configured for connection to the respective circuits formed by traces 202/204, 206/208, and 210/212. The sensing device can be programmed to monitor one or more characteristics or properties of the circuits (e.g. resistance) to determine whether a user has contacted a circuit. For example, if a user contacts traces 202 and 204 simultaneously, the monitoring device can sense the resulting drop in resistance across traces 202 and 204 and interpret the change as input data. Of course, other properties such as capacitance, conductance, inductance, and the like may be monitored in addition to or instead of resistance. Furthermore, although in the examples herein, the user interaction forms a "short" in a circuit, the actual detection may be more complex than simply determining presence or absence of a short. For example, a circuit may comprise more than two traces, with the point of user interaction being determined based on evaluating various aspects of the circuit. As another example, a circuit or portion thereof may have one or more connections to a monitoring device (or devices).

Since input data can be provided via monitoring circuits, monitoring device 110 can be configured to provide varying degrees of interactivity. For instance, the monitoring circuits may be configured as controls for monitoring device 110. As shown in FIG. 3, labels 200 are visible near the shaped regions formed by traces 202/204, 206/208, and 210/212, which indicate that in this example, button-shaped region formed by 202/204 comprises a "silence" button; the "down" arrow formed by traces 206/208 comprises a "volume down" button; and the "up" arrow formed by traces 210/212 comprises a "volume up" button. The buttons may be used for a caregiver or user of the garment to control alarms or other feedback provided by monitoring device 110. For example, monitoring device 110 may be configured to provide audible feedback such as recorded speech, music, and/or sound effects based on various conditions. The buttons illustrated in this example may be used to control the volume of the feedback. Furthermore, in some embodiments, combinations of buttons may be used to provide additional commands. For instance, if the "silence" button is held down, the "up" and "down" buttons may be used to select a particular type of audible feedback.

However, the type of feedback provided by monitoring device 110 is not limited to auditory feedback only. Instead, any suitable feedback can be provided. For instance, in addition to or instead of auditory feedback, monitoring device 110 may provide visual, tactile, and other feedback. As an example, training pant 20' shown in FIG. 10 includes several visual features visible at outer cover 40'. In this example, the visible features include lion 302, turtle 304, and baseball 306. As was noted above, visible features may be formed on and/or may otherwise be visible through outer cover 40. Additionally or alternatively, some or all of the visible features (or parts thereof) may be active features. An "active feature" generally includes any visible feature whose visible characteristics are not static. For example, animation may be provided through the use of electrochromic display principles, or parts of the visible features may be illuminated using LED or other lighting. As an example, embodiments of articles comprising active features provided using electrochromic displays are discussed U.S. Patent Application Publication No. US 2005-0137542. The active features (whether provided by electrochromic displays or otherwise) may be controlled by separate components or may be controlled via monitoring device 110. Other active features may respond to changes in temperature or chemical characteristics, such as features that appear, disappear, or change color when the diaper is wet.

As an example of feedback, monitoring device 110 may provide one or more forms of audio and visual effects, such as by playing back a lion sound effect or character voice while illuminating or animating lion 302 or parts thereof such as the lion's tail or baseball bat. Another example of feedback is tactile. For instance, monitoring device 110 may include suitable components to provide a vibrating effect such as can be found on cellular telephones in order to provide a "silent" alarm. Additionally, in some embodiments, monitoring device 110 may comprise a signaling device to wirelessly communicate with one or more remote devices to provide feedback in the form of data.

In some embodiments, feedback provided by monitoring device 110 may depend on the internal state of the article as determined by one or more internal sensors. For instance, interactivity such as device control and alarm may relate to the wetness or other internal status of the article. Although in the examples herein monitoring device 110 provides monitors both internal and external circuits, the internal circuits could be monitored using a separate device that is linked to monitoring device 110 through, e.g. additional traces. However, a monitoring device 110 that can monitor both internal and external circuits and sensors may advantageously reduce the complexity of the absorbent product. Wetness or other status of the article may be determined in any suitable way. For instance, as will be discussed in the examples below, monitoring device 110 may further connect to one or more sensors internal to an absorbent article in order to determine whether the article is wet.

Depending on the configuration of the circuit(s) (if any) internal to the absorbent article, the ends of the monitoring circuits disposed on the outside of the article may be positioned proximate to the pads or other endpoints of the internal circuits. For instance, as shown in FIGS. 8-9, the ends of traces 202, 204, 206, 208, 210, and 212 (i.e. respective pad areas 203, 205, 207, 209, 211, and 213) are generally in the same area as the ends of conductive elements 100 and 102. As depicted in the examples above, the ends of conductive elements 100 and 102, and/or any or all of traces 202 through 210 may be formed into and/or attached to pads to provide for improved connection to monitoring device 110.

For instance, the principles regarding the use of conductive pads for conductive elements, configuration of monitoring devices, and connection types for monitoring devices set forth in the above-incorporated application Ser. No. 11/405,263 may be applied to provide for achieving a good connection to the external monitoring circuits. The particular type or arrangement of connection between monitoring device and conductive traces is not intended to be limiting so long as the connection is robust enough for acceptable operation of the device.

Examples of different attachment mechanisms between the conductive pad members and the monitoring device and the particular construction of the pad member for each embodiment will now be described in detail. In these examples pad member 104 and 106, corresponding to internal conductors 100 and 102, respectively, are shown. Additionally, the examples depict pad member 203, corresponding to trace 202, and pad member 205, corresponding to trace 204. Of course, it will be recognized that more or fewer pad members could be connected using similar principles. Additionally, similar principles could be applied in embodiments in which pads are of minimal size or are nonexistent. For example, conductive traces on the exterior of the article could be connected directly to corresponding terminals on a properly-aligned monitoring device.

Figure 13:
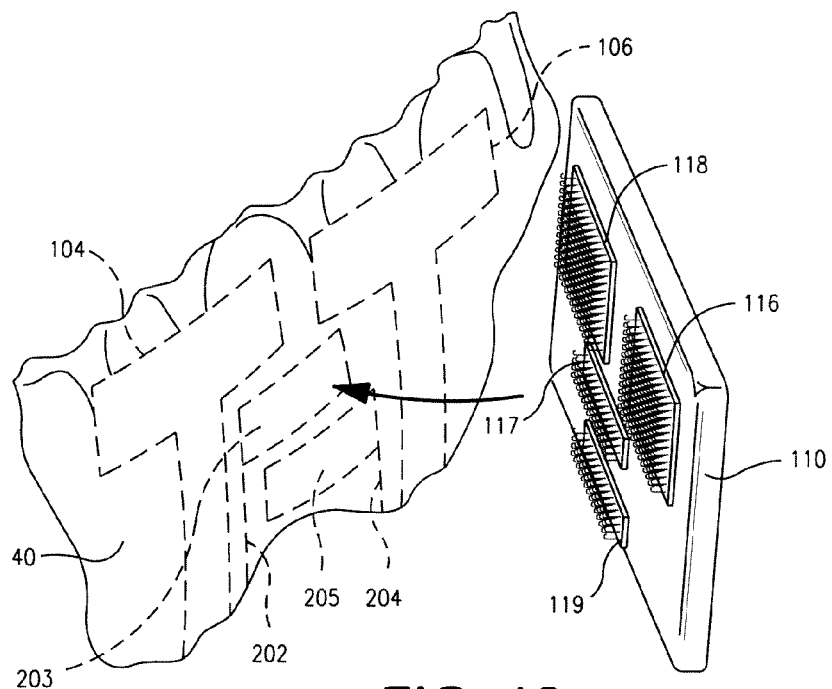
FIGS. 13, 14, 15, 16, and 17 are each a perspective view of an exemplary embodiment of an attachment mechanism suitable for attaching a monitoring device to an absorbent article.

In one embodiment, for instance, as shown in FIG. 13, the pad members 104, 106, 203, and 205 may comprise a conductive loop-type material for making a hook and loop-type connection with the monitoring device. For example, as shown, the conductive pad members 104, 106, 203, and 205 comprise a loop-type material, while the monitoring device 110 includes corresponding terminals 116, 118, 117, and 119 that comprise a hook-type material. As used herein, a loop-type material refers to any material capable of forming an attachment with a hook-type material. In this embodiment, the conductive pad members may comprise, for instance, a conductive nonwoven material or a conductive woven material, such as a conductive knitted material. The loop-type material used to form the pad members may be made electrically conductive using various techniques. For instance, in one embodiment, the loop-like material may be made from polymer fibers or filaments that contain a conductive material, such as carbon.

In an alternative embodiment, the loop-type material may be made conductive by incorporating conductive threads, such as metal threads and fibers into the formation of the material. In still other embodiments, the loop-like material may be sputter coated in order to render the material conductive. For instance, the material may be sputter coated with silver or copper. In still other embodiments, the polymers used to form the loop-type material may be doped with a conductive material in any suitable manner in addition to as described above.

The hook-type material used to form the terminals 116, 118, 117, and 119 of the monitoring device 110 may also be rendered conductive using any of the above techniques. In one particular embodiment, for instance, each of the hooks contained on the hook-type material may be made from a metal.

Commercially available conductive hook-type material and loop-type material may be obtained, for instance, from Fastech of Jacksonville, Fla., which offers hook and loop tapes that are coated with silver. Other conductive hook and loop materials are available from NC Stat Corporation, from Bio-Logic Systems Corporation and from Velcro Industries B.V.

In this embodiment, the conductive pad members 104, 106, 203, and 205 may be present at the surface of the absorbent article for making a connection with the monitoring device. Alternatively, some or all of the conductive pad members may be present below the surface. In this embodiment, an opening may be made in the overlying material in order to make a connection. Alternatively, the overlying material may include perforations or be sufficiently porous for a hook and loop attachment to be made through the material.

Figure 14:
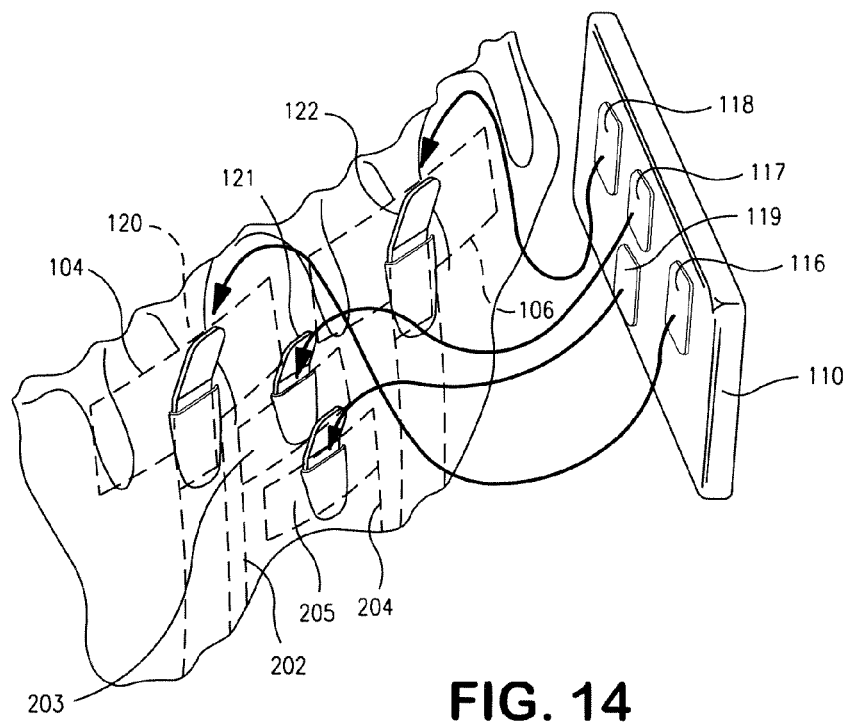

Referring to FIG. 14, another embodiment of an attachment mechanism for attaching the conductive pad members 104, 106, 203, and 205 to the respective terminals 116, 118, 117, and 119 on the monitoring device 110 is shown. In this embodiment, the pad members 104, 106, 203, and 205 are electrically connected to a respective conductive tab member 120, 122, 121, and 123. As illustrated, the first terminal 116 and the second terminal 118 on the monitoring device 110 comprise corresponding slots or pockets that are configured to receive the conductive tab members 120 and 122. In this manner, electrical connection is made between the monitoring device 110 and the pad members 104 and 106. Similarly, the third terminal 117 and the fourth terminal 119 on the monitoring device 110 comprise corresponding slots or pockets that are configured to receive the conductive tab members 121 and 123. Terminal 117 is thereby connected to pad member 203 through tab member 121, and terminal 119 is thereby connected to pad member 205 through tab member 123.

In some embodiments, some or all of the conductive pad members may be embedded within the chassis 32, for instance, below at least one layer of material. The corresponding conductive tab members can penetrate the outer layers to make an electrical contact with the terminals of monitoring device 110. The conductive pad members can be made from various materials. For instance, the pad members can be made from any of the materials described above with respect to the embodiment illustrated in FIG. 13. Alternatively, the pad members may comprise other conductive woven or nonwoven fabrics that may not be suitable as a loop-type material.

In addition to woven and nonwoven fabrics, the pad members may also comprise a conductive film. For instance, the pad members may comprise a metal foil or an otherwise conductive film. In one particular embodiment, for instance, the pad members may comprise a conductive mylar film. In an alternative embodiment, the pad members may comprise a conductive ink printed on a layer of material that forms the chassis or a conductive adhesive applied to one of the materials that comprises the chassis. As was noted previously, at least the conductive pad members corresponding to conductive traces may be printed on the exterior of the article in some embodiments.

In still another embodiment of the present invention, the conductive pad members may be embedded within the chassis 32 below at least one layer of material. The material covering the pad members may comprise a suitable loop-type material for making a hook and loop attachment. For example, in one embodiment, the overlying layer of material may comprise a nonwoven web, such as a spunbond web.

In this embodiment, the monitoring device may include conductive terminals that comprise a hook-type material as shown in FIG. 13. The hook-type terminals may be configured to attach to the layer of material that covers the pad members. The layer of material, however, may be sufficiently porous to allow the individual hooks not only to engage the layer but also to penetrate through the layer and make an electrical connection with the conductive pad members. Thus, in this embodiment, the terminals on the monitoring device attach to a nonconductive layer in a manner that still provides an electrical connection with the conductive pad members.

Figure 15:
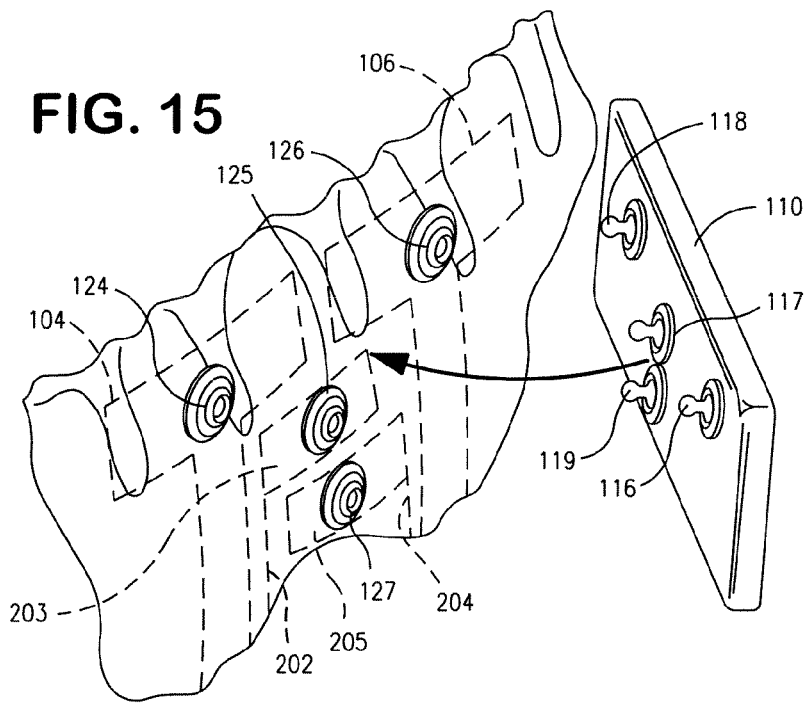

Referring to FIG. 15, still another embodiment of an attachment mechanism in accordance with the present invention is shown. In this embodiment, each of the conductive pad members 104. 106, 203, and 205 are electrically connected to a prong receiving member 124, 126, 125, and 127, respectively. As shown, the monitoring device 110 includes corresponding prongs 116, 118, 117, and 119 that serve as the first, second, third, and fourth terminals. The prongs are configured to snap in place into the prong receiving members. In one embodiment, the prong receiving members may be located below one or more layers of material. The prongs disposed on the monitoring device 110, on the other hand, are configured to pierce the overlying layers of material in order to form an electrical connection with the prong receiving members.

Alternatively, openings may be formed in the overlying material so that the prongs may be inserted through the openings in the overlying material and engage the prong receiving members. It should be understood that, in the embodiment illustrated in FIG. 15, the prong receiving members and the prongs may have any suitable shape in order to attach together. For example, the present disclosure is intended to cover any suitable male-female connections.

Figure 16:
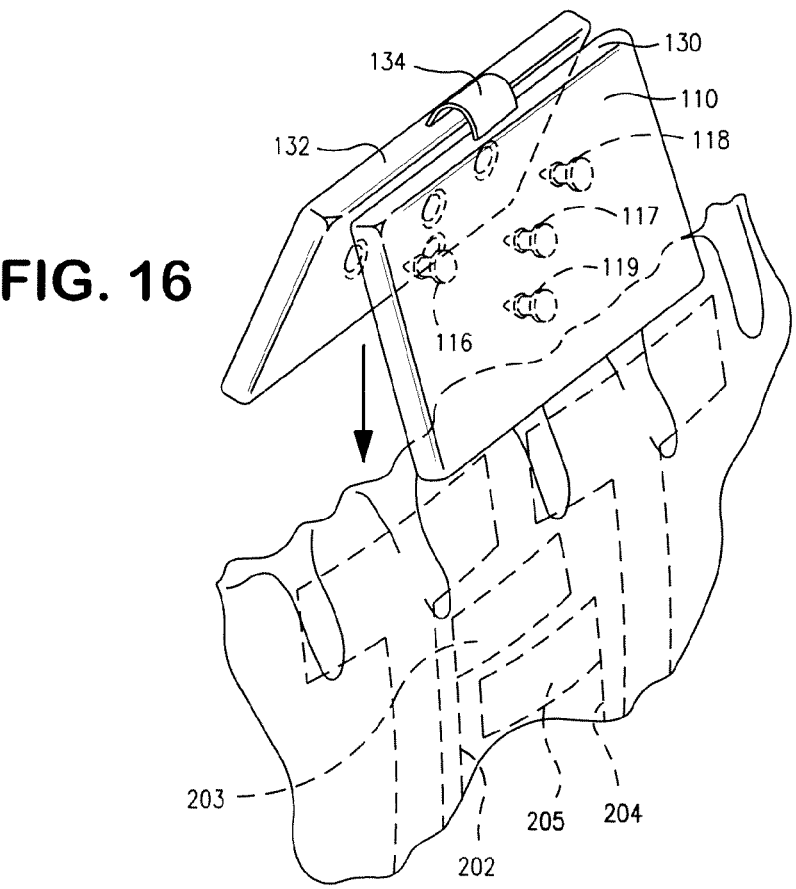

Referring to FIG. 16, another embodiment of an attachment mechanism that may be used to attach a monitoring device to the open circuit contained in the absorbent article is shown. In this embodiment, the monitoring device 110 comprises a clip device including a first plate 130 spaced from a second plate 132. More particularly, an end of the first plate 130 is pivotally connected to an end of the second plate 132 about a hinge 134.

In order to make an electrical connection with the conductive pad members 104, 106, 203, and 205, the first plate 130 includes four prongs that serve as the first terminal 116, the second terminal 118, the third terminal 117, and the fourth terminal 119.

As shown in the drawing, the plates 130 and 132 of the monitoring device 110 are configured to be placed over an edge of the chassis and brought together such that the prongs 116, 118, 117, and 119 pierce the chassis and lock into place. Specifically, the prongs are intended to pierce the chassis where the pad members are located in order to make an electrical connection with the pad members. Of course, if any of the pads (such as 203 and 205, for instance) are located at the surface, the corresponding prongs may not need to fully pierce the chassis (or pierce the article at all). This embodiment provides various advantages and benefits. In particular, in this embodiment, the pad members can be located at any position within the chassis and still be contacted with the prongs. In this embodiment, the prongs can pierce through the entire thickness of the chassis or may only partially penetrate the chassis in order to make a connection with the pad members.

Other embodiments of various clip devices that may be used as a monitoring device are illustrated and discussed in further detail in the above-referenced application Ser. No. 11/405,263. For instance, a monitoring device 110 can comprise a clip device including a first plate 130 spaced from a second plate 132. The plates 130 and 132 can be are biased towards each other by a spring positioned about a hinge. The monitoring device 110 can be designed to be placed over an edge of an absorbent article in accordance with the present disclosure.

In some embodiments, the terminals may comprise prongs, with each prong comprising one or more pointed teeth, blades, pins, and/or other suitable structures that are configured to not only hold the monitoring device in position but also to penetrate the chassis (if necessary) and make an electrical connection with the pad members. It should be understood, however, that the number and placement of teeth, pins, blades and other structures may vary and may be positioned according to any suitable pattern.

If desired, one or more of the plates may further include one or more backing members. The backing members can be positioned so as to be located opposite the prongs. The backing members can be made of any suitable material capable of receiving the prongs should the prongs extend all the way through the chassis. The backing members, for instance, can be made from any suitable elastomeric material, foam material or polymeric material.

Figure 17:
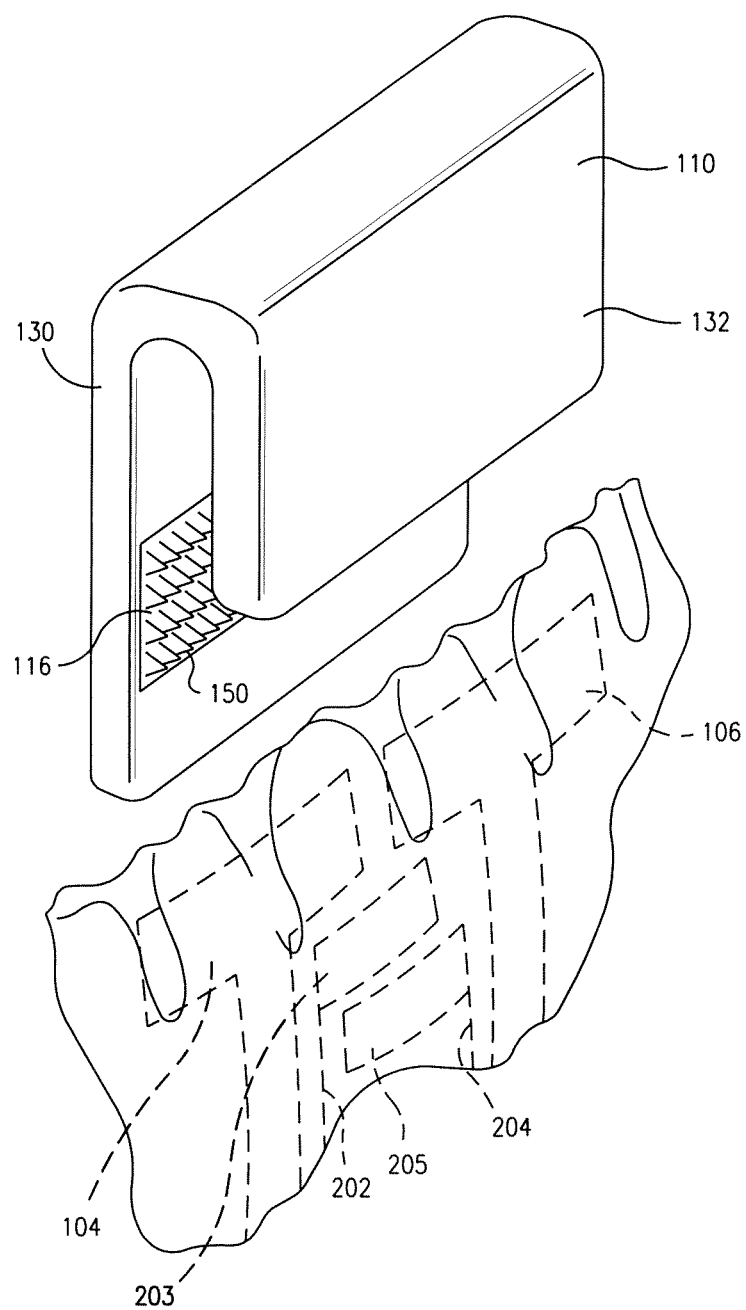

Referring to FIG. 17, still another embodiment of a monitoring device 110 is shown. In this embodiment, the monitoring device 110 includes a clip device comprising a first plate 132 spaced from a second plate 130. The plates 132 and 130 are integral with each other and are made from a flexible material that allows the plates to be separated from each other for placing the monitoring device over an edge on an absorbent article. Once the plates, however, are placed on the absorbent article, the plates are biased towards each other for holding the monitoring device in place. In this manner, the monitoring device 110 has a paper clip-like structure.

In the embodiment illustrated in FIG. 17, the monitoring device 110 can be made from any suitable material. For example, in one embodiment, the monitoring device can be made from a flexible plastic material. It should be understood, however, that elastomeric materials and metal materials may also be used.

Similar to the embodiment shown in FIG. 16, the monitoring device 110 includes a first terminal 116 and second, third and fourth terminals (not shown). Each terminal can be comprised of a plurality of teeth 150 that are positioned so as to make an electrical connection with a corresponding pad member when the monitoring device is aligned on the article. In clip-like embodiments, the positioning of the conductive pads and the terminals in the monitoring device may be varied so that when positioned on the article the monitoring device can achieve a good connection. For instance, the conductive pad members may be positioned lower on the article and the terminals may be positioned lower on the monitoring device so that the device can connect to the circuit(s) comprised in the article without interference from, e.g., an elastic waistband of the article.

In some embodiments, the article and/or monitoring device can include one or more features to help aid in proper alignment and connection of the monitoring device to the article. For example, in some embodiments, one or more circuits within the article can be formed so that proper alignment can be evaluated. For instance, internal circuits (such as wetness sensors) may be formed so as to have an expected impedance that can be verified by the monitoring device. In other embodiments, one or more circuits dedicated to verifying connections can be included. Indicia visible on the article and/or monitoring device may also be used to facilitate proper alignment. Aspects of ensuring alignment in this manner are discussed in presently co-pending U.S. patent application Ser. Nos. 11/412,351 and 11/412,364, each filed Apr. 26, 2006 and which are each entitled WETNESS MONITORING SYSTEMS WITH STATUS NOTIFICATION SYSTEMS, as well as U.S. patent application Ser. No. 11/444,847, filed May 31, 2006 and entitled ALIGNMENT AIDS FOR A SENSING ARTICLE. The '351, '364 and '847 applications are each hereby incorporated by reference in their entireties to the extent such applications are not in conflict with the present subject matter.

Additionally, the size of the control areas can be varied through the use of different trace patterns and widths. For example, for an elder care product, larger controls may be advantageous for use by persons with poor sight or motor control. The larger controls regions may be coextensive with larger printed labels, control area designators, and the like.

Figure 11A:
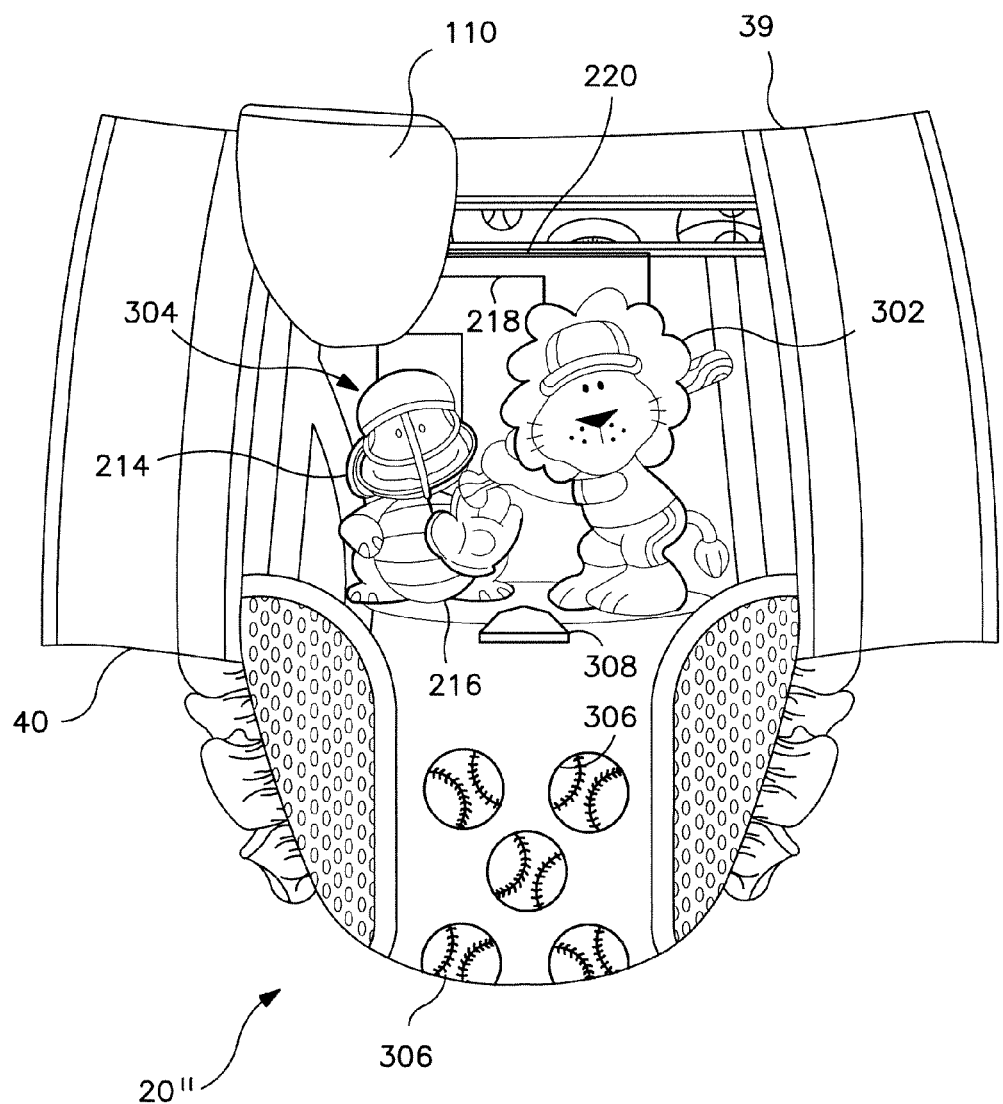
FIG. 11A is a front view of yet another exemplary absorbent article made in accordance with the present subject matter.
Figure 11B:
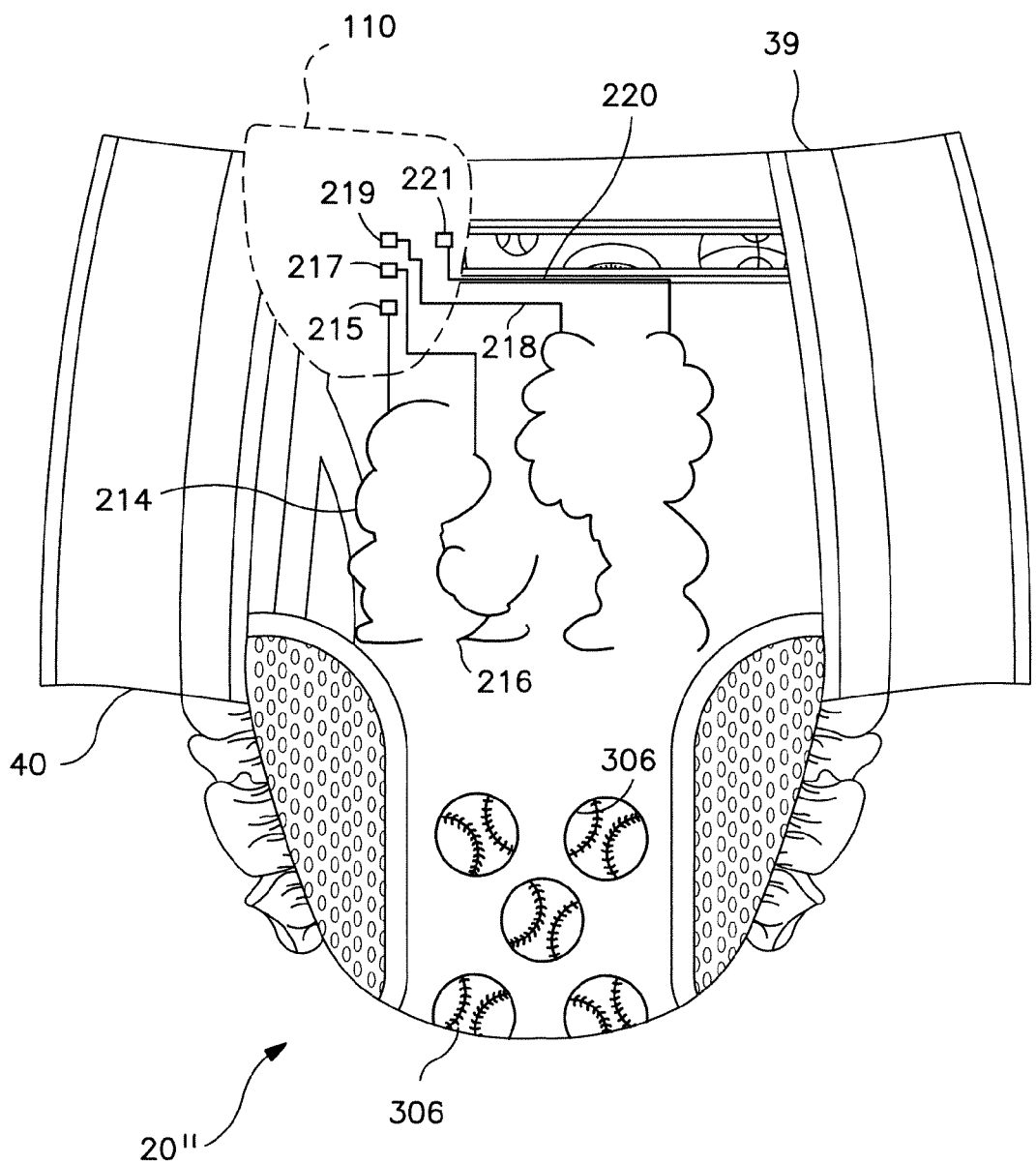
FIG. 11B is an alternative front view of the exemplary absorbent article shown in FIG. 11A.

Turning now to FIGS. 11A and 11B, the exterior of another absorbent article (in this case, training pant 20") is shown in a front side view. In this example, monitoring device 110 is carried by the article and is connected to two monitoring circuits formed on the exterior over of the training pant. FIG. 11A shows a full exterior view of the article and monitoring device, while in FIG. 11B the characters and monitoring device are omitted to reveal the full extent of the circuit traces and pads.

Each circuit comprises traces that correspond to different regions of the exterior, and in this example, each region corresponds to a character provided as a visual feature visible at the exterior of the garment. The first circuit, comprising traces 214 and 216, covers the outline of turtle character 304. The second circuit, comprising traces 218 and 220, covers the outline of lion character 314. Each trace 214, 216, 218, and 220 is connected to a respective corresponding pad member 215, 217, 219, and 221 (visible in FIG. 11B).

In this example, the other visual features including home plate 308 and baseballs 306 do not have corresponding trace outlines for purposes of clarity. Any or all of the visual features may be fixed (e.g., printed) or may partially or fully comprise active features. The first and second circuits may be used to provide input to monitoring device 110. For instance, a user of the undergarment may provide input as part of an interactive game. As another example, the caretaker of a user of the undergarment may use the characters to provide feedback by triggering a response from device 110.

A great variety of interactive features can be provided by programming or otherwise configuring monitoring device 110 to respond to conditions including the status of one or more circuits on the exterior of the garment. For example, as noted above, the monitoring device may be configured to provide one or more interactive games to amuse, educate, and/or otherwise occupy the wearer of the garment. An "interactive game" is meant to refer to any set of one or more parameters defining outcomes based on receipt (and/or non-receipt) of data. The type and complexity of the game can vary, and may differ between modes of operation (e.g. simple matching games for infants, more complex games for adult users).

For instance, device 110 shown in FIGS. 11A and 11B may provide a matching game whereby the wearer of the garment is prompted to select a specified character or other visual feature. If the user selects the correct feature (i.e. by providing input by changing the characteristic of the circuit associated with the feature) than the monitoring device may provide feedback keyed to the character.

For example, monitoring device 110 may use an audio recording or generated voice to prompt a child wearing disposable pant 20 to "find the lion". If the child touches the region comprising lion 302 so as to change the characteristics of the circuit formed by traces 218/220, the monitoring device may provide feedback such as the voice of the lion character saying, "that's right." On the other hand, if the child selects turtle 304 in response to the prompt, the monitoring device may play back the turtle's voice saying, "try again." Of course, the interactive game could be more complex depending on the developmental level of the child and/or the number of characters and input options. As another example, a more complex game may involve animating multiple visible features of the article and monitoring for input data that indicates action. For example, baseballs 306 may be animated in sequence timed so that if a user selects lion 302 in time (e.g. by changing a characteristic of the circuit formed by traces 218/220, a "hit" is scored.

External monitoring circuits may also be used to provide input data to provide advanced control and configuration features. Toilet training is one example of advanced control features/feedback that can be provided by a monitoring device 110. For instance, the caregiver may be able to select a control to provide reinforcement to the child wearing the article. For example, the caregiver may select a region of the article to play a message such as "accidents happen." Alternatively, if the caregiver determines that the child has avoided an accident, then the caregiver may select a different region of the article to play a message such as "good job." The messages may be accompanied by other feedback, such as animation or illumination of active features on the article. For instance, if the article features a character, the reinforcement message(s) may be matched to the character.

Additional aspects of toilet training based on the use of monitoring devices are discussed in U.S. patent application Ser. No. 11/540,418, filed Sep. 29, 2006 and entitled SENSOR AND ASSOCIATED ARTICLES FOR TOILET TRAINING, which is hereby incorporated by reference herein to the extent it is not inconsistent with the presently-discussed subject matter. User input received via one or more monitoring circuits as discussed herein may be used to configure, control, and otherwise further enhance the toilet training process as discussed in the above-noted application.

In some embodiments, potty training can be further enhanced through tracking of events based on recording internal sensor data and classifying the data based on user input. For instance, as noted above, the monitoring device can be configured to detect a wetness event and provide feedback based on the caregiver's selection of a region of the article. The selection of a region may further trigger recording of the event for tracking toilet training progress. For instance, selection of the "good job" region may direct the monitoring device to record the time of the successful toilet event. Correspondingly, selection of the "accidents happen" option may direct the monitoring device to record the time of the wetting event and the status of the wetting sensor(s).

Of course, the recording features may be implemented separately from feedback/reinforcement features. For instance, an adult incontinence product may simply support recording of wetting events at the time such events occur or may require user confirmation before recording.

In some embodiments, monitoring device 110 may be configured to "unlock" interactivity and functionality based on the degree of progress in toilet training. For instance, assume that the article includes a monitoring circuit corresponding to home plate 308 in addition to circuits corresponding to lion 302 and turtle 304. Monitoring device 110 could be configured to provide a progressive game wherein the degree of interactivity varies based on the level of toilet training that has been achieved. For instance, only one character (such as lion 302) may be interactive if a child is at an initial training level. Then, as the child progresses (as measured by, for example, lack of wetting events), more characters could become interactive.

Generally speaking, any suitable level and type of feedback provided using monitoring device 110 and the absorbent article. For instance, feedback during toilet training may be dynamically controlled via algorithms that evaluate recorded events in light of past feedback, the length of time training has occurred, and/or other data to determine which type(s) of feedback are leading to success and which types are not advancing the toilet training process. The operational parameters of the smart algorithm(s) may be fine-tuned or otherwise configured based on user input data provided via one or more monitoring circuits on the exterior of an article.

Figure 12:
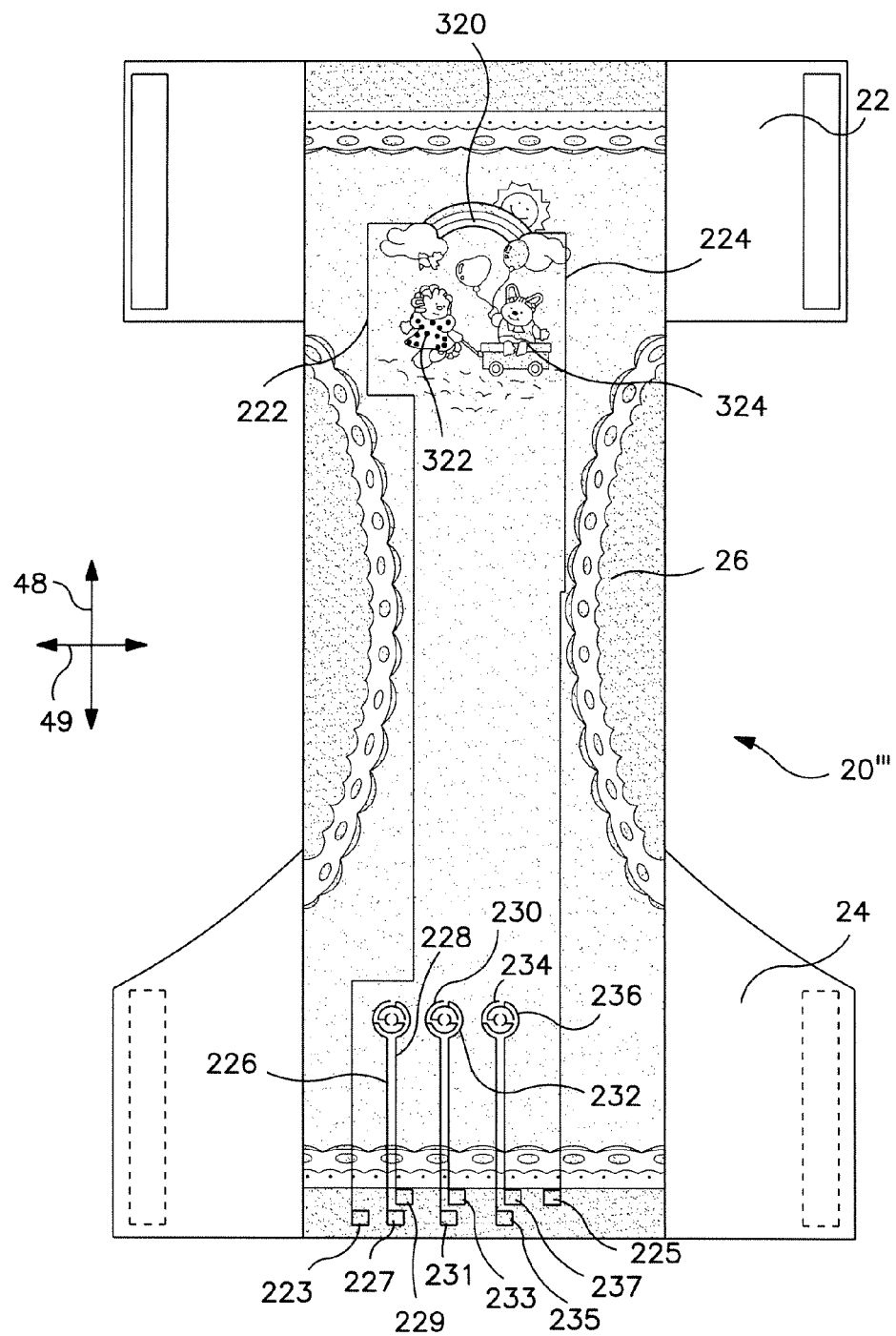
FIG. 12 is a plan view of a still further exemplary absorbent article with the article in an unfastened, unfolded, and laid flat condition showing the surface of the article that faces away from the wearer.

FIG. 12 illustrates another exemplary article in a laid-flat arrangement showing the exterior of the article, in this example, a training pant 20'''. Training pant 20''' includes a front region 22, crotch region 26, and back region 24. Various features are printed on or are otherwise visible at the exterior of training pant 20''', including rainbow 320, character 322 and character 324. Any or all of the visible features may be active features (e.g. animated). In this example, training pant 20''' features four monitoring circuits formed on the exterior of the article. One circuit comprises traces 222 and 224, which are formed to correspond to the region of rainbow 320. Traces 222 and 224 extend from the front side 22 of article 20''' through crotch region 26 to back region 24 where respective pads 223 (for trace 222) and 225 (for trace 224) aid in connection of a monitoring device 110 (not shown). As was noted above, monitoring device 110 may be configured to monitor the circuit formed by traces 222/224 for changes in one or more characteristics that indicate user interaction.

Article 20''' further includes three monitoring circuits formed at the back of the article, namely button-shaped regions comprising traces 226/228, 230/232, and 234/236. For instance, a monitoring device 110 may be configured to receive caregiver or other input from the button-shaped regions. Traces 226, 228, 230, 232, 234, and 236 are also connected to respective pads 227, 229, 231, 233, 235, and 237 for aid in connection to monitoring device 110. The visibility of the traces may vary, as was noted above. For instance, portions of traces 222 and 224 proximate rainbow 320 may be formed to outline or blend in with the colors of rainbow 320, while other portions of traces 222 and 224 (such as the portions extending through crotch region 26) may be formed of transparent conductive ink or may be formed of one or more colors that blend in with the other visual features of article 20''' in that area.

Other interactive features may be used to enhance interaction between users of the article, such as interactions between a wearer of an undergarment/diaper and the wearer's caregiver. For example, as noted above, the absorbent article may include one or more internal wetness sensors. If the article comprises a diaper, the monitoring device 110 may provide a range of alarm options that are selectable by interaction with controls formed by circuits on the exterior of the article. For instance, the volume and/or type of alarm can be varied by the caregiver for different situations, such as silencing the alarm when in public areas, increasing the volume when the caregiver is in a noisy environment or is unlikely to hear an alarm, and the like.

As indicated above, the monitoring device 110 is configured to provide different levels or types of interactivity based on the age or training level of the wearer of an article. For instance, a single type of monitoring device 110 may be provided for use in a range of different absorbent articles intended for different users. As an example, a manufacturer may desire to use a single type of monitoring device (or limited number of types of devices) for use across one or more ranges of absorbent articles with sensing capability. However, this practice can lead to less than optimal user experiences.

The desired functionality of the monitoring device 110 may be accessed by the user by selecting the appropriate hardware, software, and/or firmware version. For instance, in one embodiment, the monitoring device may only need firmware updates to perform the desired functionality of any age group (i.e., from newborn to elderly). However, in another embodiment, the hardware or interface would simply need to be changed or manipulated to achieve the desired functionality.

As noted above, the monitoring device may evolve by utilizing firmware updates. Firmware, as the name suggests, is a middle-ground between hardware and software. Like software, firmware is a computer program which is executed by a microprocessor or a microcontroller. However, firmware is also tightly linked to a piece of hardware. Essentially, firmware is the programmable content of a hardware device. Since firmware is tightly linked to its hardware, the firmware can be updated post-manufacturing, either electronically, or by replacing a storage medium such as a socketed memory chip.

When utilized in the present invention, firmware updates have the ability to lock/unlock the desired user features. For example, the monitoring device may be connected to an external source (e.g., a computer) and download updates to replace existing firmware. In one embodiment, the device is powered by a rechargeable cell and a docking station may be utilized for charging and firmware downloading.

For example, the monitoring device may be configured to provide different types of wetness notification messages that are not appropriate for all users. As an example, for an infant, a beep or other notification intended to alert a caregiver of a wet diaper may be appropriate. A more interactive message of "oops, you made a mistake" may be entirely appropriate for a toddler wearing a training pant. However, the same message may be insulting to an adult wearing an incontinence product. Therefore, monitoring device 110 may be configured by aforementioned methods to select an appropriate level of interactivity based on user input provided through the external monitoring circuit(s). For example, a user can select a mode of operation that is appropriate for the contemplated use of the article.

Modes of operation may restrict some monitoring device functionality. For instance, interactive/toilet training reinforcement features of monitoring device 110 may only be activated if selected by a user and may otherwise be disabled. As another example, advanced control features (such as device reset) or feedback options may be disabled for certain types of users to avoid misuse or accidental reconfiguration of monitoring device 110. For instance, a user of an infant product may select a relatively "low" level of interactivity that disables features such as games and feedback unrelated to the wetness (or other state) of an article. The monitoring device may support security features, such as a lock or password, to prevent unauthorized reconfiguration or access to features of the device.

As described, the monitoring device of the present invention may be useable over a complete human lifespan. Thus, with such a long product lifespan, it may be necessary for the user to conduct regular backups of the data. In one embodiment of the invention, the monitoring device may be electrically connected to an external storage device such as a computer in which regular backups of data could be made in case the device is lost or broken. With regular backups, a new monitoring device may progress from the last backup point of the lost or broken monitoring device.

Modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims.

What is claimed is:

1. A method for monitoring physiological indices in an individual as the individual ages comprising:
   associating one or more signaling devices with absorbent articles worn by the individual, each absorbent article including at least one sensing device that senses a physiological indication related to the individual, the sensing device being placed in communication with the one or more signaling device when the absorbent article is being worn,
   inputting physiological information into the one or more signaling devices regarding the individual, wherein the physiological information comprises information about the age of the individual; and
   updating at least one function or display of the one or more signaling devices via communication with an external device as the individual reaches new developmental stages throughout the life of the individual, wherein the developmental stages comprise a newborn stage, a toddler stage, an adolescent stage, and an adult stage, wherein the update in the function or display output is associated with the same physiological indication but with a different type of interactivity with the individual based on the developmental stage.

2. The method as set forth in claim 1, further comprising the step of recording information on the one or more signaling devices received from the sensing device and storing the information on non-transitory electronic storage medium as the individual increases in age, the stored information being used to update the at least one function or display.

3. The method as set forth in claim 1, wherein the at least one function or display is configured to be updated by a user changing non-transitory software, hardware, or firmware contained in the one or more signaling devices.

4. The method as set forth in claim 1, wherein the function of the one or more signaling devices is to indicate wetness in the absorbent articles initially and then is updated to further indicate void frequency, void amounts, or an estimated wetness event as the individual increases in age.

5. The method as set forth in claim 1, wherein the function of the at least one sensing device is to sense wetness in the absorbent articles initially and then is updated to detect anemia or the presence of a material including a yeast or a component in urine, menses, or blood.

6. The method of claim 5, wherein the component detected is at least one of a polysaccharide, sugar, or protein.

7. The method as set forth in claim 1, wherein the external device is capable of changing non-transitory software or firmware contained in the one or more signaling device.

8. The method as set forth in claim 7, wherein the one or more signaling device is connected to the external device utilizing at least one of a wired or wireless connection.

9. The method of claim 1, further comprising the step of connecting the one or more signaling device to a docking station, the docking station configured to charge a rechargeable cell in the one or more signaling device.

10. The method of claim 9, wherein the docking station is configured for receiving non-transitory software or firmware, further wherein the docking station is configured to allow a user to change the non-transitory software or firmware contained in the one or more signaling device.

11. A monitoring device for use with an absorbent article worn by an individual, the monitoring device comprising:
at least one signaling device comprising at least one of hardware, non-transitory software, or firmware, wherein physiological information regarding the individual is input into the at least one signaling device, wherein the physiological information comprises information about the age of the individual;
at least one sensing device configured to sense a physiological indication related to the individual, the at least one sensing device electrically connected to at least one monitoring circuit in the absorbent article and being placed in communication with the one or more signaling device,
an external device configured to communicate with the at least one signaling device and update at least one function or display of the at least one signaling device as the individual reaches new developmental stages throughout the life of the individual, wherein the developmental stages comprise a newborn stage, a toddler stage, an adolescent stage, and an adult stage, wherein the update in the function or display is associated with the same physiological indication but with a different type of interactivity with the individual based on the developmental stage.

12. The monitoring device of claim 11, wherein the absorbent article comprises a diaper, training pant, incontinence product, or feminine hygiene product.

13. The monitoring device of claim 11, wherein the at least one sensing device is configured to receive input data from the individual by monitoring for a change in a characteristic of the at least one monitoring circuit.

14. The monitoring device of claim 11, wherein the external device is capable of storing data.

15. The monitoring device of claim 11, wherein the external device is a computer.

16. The monitoring device of claim 11, wherein the external device is a docking station, the docking station configured to charge a rechargeable cell in the monitoring device.

17. The monitoring device of claim 11, wherein the at least one sensing device senses at least one of absorbent article wetness, void frequency, void amounts, activity level, physical position of the article wearer, or physical location of the article wearer.

18. The monitoring device of claim 11, wherein the at least one sensing device detects anemia or the presence of a material including a yeast or a component in urine, menses, or blood.

19. The monitoring device of claim 11, wherein the at least one signaling device comprises non-transitory software or firmware, the non-transitory software or firmware comprising an algorithm capable of receiving inputs from the individual and creating a predictive model for training.

20. An absorbent article comprising the monitoring device of claim 1, the absorbent article including a chassis comprising an outer cover, the outer cover having an interior surface and an exterior surface, and an absorbent structure positioned adjacent the interior surface of the outer cover, the chassis including a crotch region positioned in between a front region and a back region.

* * * * *